United States Patent
Gabriel et al.

(10) Patent No.: US 6,747,053 B2
(45) Date of Patent: *Jun. 8, 2004

(54) HETEROARYL NITRILES

(75) Inventors: Tobias Gabriel, San Francisco, CA (US); Nancy Elisabeth Krauss, Mountain View, CA (US); Taraneh Mirzadegan, Los Altos, CA (US); Wylie Solang Palmer, Mountain View, CA (US); David Bernard Smith, San Mateo, CA (US)

(73) Assignee: Roche Palo Alto LLC, Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/308,963

(22) Filed: Dec. 3, 2002

(65) Prior Publication Data

US 2003/0212097 A1 Nov. 13, 2003

Related U.S. Application Data

(60) Provisional application No. 60/336,750, filed on Dec. 4, 2001.

(51) Int. Cl.[7] ..................... A61K 31/404; C07D 209/12
(52) U.S. Cl. ................. 514/419; 548/492; 548/490; 548/180; 546/169; 546/171; 514/311; 514/367
(58) Field of Search ................. 514/419, 311, 514/367; 548/492, 490, 180; 546/169, 171

(56) References Cited

U.S. PATENT DOCUMENTS

| | | | |
|---|---|---|---|
| 5,691,321 A | 11/1997 | Schaper et al. | |
| 6,462,076 B2 * | 10/2002 | Gabriel et al. | 514/463 |

FOREIGN PATENT DOCUMENTS

| | | |
|---|---|---|
| DE | 2624290 A1 | 4/1977 |
| WO | WO 98/03540 A2 | 1/1998 |
| WO | WO 99/24460 A2 | 5/1999 |
| WO | WO 01/49288 A1 | 7/2001 |
| WO | WO 01/96285 A1 | 12/2001 |
| WO | WO 03/041649 A2 | 5/2003 |

OTHER PUBLICATIONS

Brömme, "The new discoveries made regarding cysteine proteases may offer therapeutic targets for bone disease, cancer and neurodegeneration," *Drug News Perspect*, 1999, pp. 73–82, vol. 12(2).

Chapman et al., "Emerging roles for cysteine proteases in human biology," *Annu. Rev. Phys.*, 1997, pp. 63–88, vol. 59.

Tezuka et al., "Molecular Cloning of a Possible Cysteine Proteinase Predominantly Expressed in Osteoclasts," *J. Biol. Chem.*, 1994, pp. 1106–1109, vol. 269:2.

Lerner, et al, "Human Cystatin C, a Cysteine Proteinase Inhibitor, Inhibits Bone Resorption In Vitro Stimulated by Parathyroid Hormone and Parathyroid Hormone–Related Peptide of Malignancy," *J. Bone Min Res.*, 1992, pp. 433–440, vol. 7:4.

Everts, et al., "Degradation of Collagen in the Bone–Resorbing Compartment Underlying the Osteoclast Involves Both Cysteine–Proteinases and Matrix Metalloproteinases," *J. Cell. Physiol.*, 1992, pp. 221–231, vol. 150, Wiley–Liss.

Hummel, et al., "Cysteine Proteinase Cathepsin K mRNA Is Expressed in Synovium of Patients with Rheumatoid Arthritis and Is Detected at Sites of Synovial Bone Destruction," *J. Rheumatol.*, 1998, pp. 1887–1894, vol. 25:10.

Sukhova, et al., "Expression of the Elastolytic Cathepsins S and K in Human Atheroma and Regulation of their Production in Smooth Muscle Cells," *J. Clin. Invest.*, 1998, pp. 576–583, vol. 102:3.

Littlewood–Evans et al, "The Osteoclast–asociated Protease Cathepsin K Is Expressed in Human Breast Carcinoma," *Cancer Res.*, 1997, pp. 5386–5390, vol. 57.

Otto et al., "Cysteine Proteases and Their Inhibitors," *Chem. Rev.*, 1997, pp. 133–171, vol. 97.

Thompson et al., "Design of potent and selective human cathepsin K inhibitors that span the active site," *Proc. Natl. Acad. Sci. USA*, 1997, pp. 14249–14254, vol. 94.

Maubach et al, "The inhibition of cathepsin S by its propeptide," *Eur. J. Biochem.*, 1997, pp. 745–750, vol. 250:2.

(List continued on next page.)

Primary Examiner—Charanjit S. Aulakh
(74) Attorney, Agent, or Firm—Robert C. Hall

(57) ABSTRACT

The present invention relates to compound of formula (I)

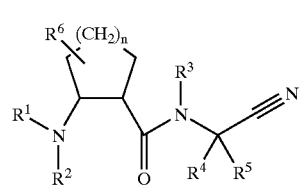

(I)

wherein $R^1$, $R^2$, $R^3$, $R^4$, $R^5$ and n are as defined in the description and claims and pharmaceutically acceptable salts and/or pharmaceutically acceptable esters thereof. The compounds are useful for the treatment of diseases which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease.

36 Claims, No Drawings

OTHER PUBLICATIONS

Rink, "Solid–phase synthesis of protected peptide fragments using a trialkoxy–diphenyl–methylester resin," *Tetrahedron Lett.*, 1987, pp. 3787–3790, vol. 28:33, Pergamon Journals.

Atkins & Burgess, "The Reactions of an N–Sulfonylamine Inner Salt," *J. Am. Chem. Soc.*, 1968, pp. 4744–4745, vol. 90:17.

Kobayashi et al., "Chiral Synthon Obtained with Pig Liver Esterase: Introduction of Chiral Centers into Cyclohexene Skeleton," *Chem. Pharm. Bull.*, 1990, pp. 350–354 vol. 38:2.

Davies, et al., "Asymmetric Synthesis of (–)–(1R, 2S)–Cispentacin and Related *cis*– and *trans*– 2–Amino Cyclopentane– and Cyclohexane– 1–Carboxylic Acids," *J. Chem. Soc. Perkin Trans.*, 1994, pp. 1411–1415, vol. 1.

* cited by examiner

HETEROARYL NITRILES

CROSS REFERENCE TO RELATED INVENTIONS

This application claims the priority benefit under Title 35 U.S.C. 119(e) of U.S. Provisional Application Serial No. 60/336,750, filed Dec. 4, 2001, the disclosure of which is herein incorporated by reference.

BACKGROUND OF THE INVENTION

Cysteine proteases have been viewed as lysosomal mediators of terminal protein degradation. Several newly discovered members of this enzyme class, however, are regulated proteases with limited tissue expression, which implies specific roles in cellular physiology and thus would allow a specific targeting of these activities without interfering with the general lysosomal protein degragation. Development of inhibitors of specific cysteine proteases promises to provide new drugs for modifying immunity, osteoporosis, neurodegeneration, chronic inflammation, cancer and malaria (Brömme, *Drug News Perspect* 1999, 12(2), 73–82; Chapman et al., *Annu. Rev. Phys.* 1997, 59, 63–88).

Cysteine proteases can be grouped into two superfamilies: the family of enzymes related to interleukin 1β converting enzyme (ICE), and the papain superfamily of cysteine proteases. Presently there are at least 12 human proteases of the papain family from which sequences have been obtained (cathepsin B, L, H, S, O, K, C, W, F, V(L2), Z(X) and bleomycin hydrolase). Cathepsin K was first discovered as a cDNA prominent in rabbit osteoclasts and referred to as OC-2 (Tezuka et al., *J. Biol. Chem.* 1994, 269, 1106–1109). Recent observations indicate that cathepsin K is the most potent mammalian elastase yet described. Cathepsin K, as well as cathepsins S and L, are also potent collagenases and gelatinases. Macrophages appear capable of mobilizing the active proteases within endosomal and/or lysosomal compartments to the cell surface under special circumstances. In this case, the cell surface/substrate interface becomes a compartment from which endogenous inhibitors are excluded and can be viewed as a physiological extension of the lysosome. This type of physiology is an innate trait of osteoclasts, a bone macrophage, and may also be exploited by other macrophages or cells in the context of inflammation. The abundance of cathepsin K in osteoclasts leads to the suggestion that cathepsin K plays an important role in bone resorption. Studies revealed that cathepsin K is the predominant cysteine protease in osteoclasts and is specifically expressed in human osteoclasts. A correlation between inhibition of cysteine protease activity and bone resorption has been reported (Lerner et al., *J. Bone Min. Res.* 1992, 7, 433; Everts et al., *J. Cell. Physiol.* 1992, 150, 221). Cathepsin K has been detected in synovial fibroblasts of RA patients, as well as in mouse hypertrophic chondrocytes (Hummel et al., *J. Rheumatol.* 1998, 25(10), 1887–1894.). Both results indicate a direct role of cathepsin K in cartilage erosion. P. Libby (Libby et al., *J. Clin. Invest.* 1998, 102 (3), 576–583) reported that normal arteries contain little or no cathepsin K or S whereas macrophages in atheroma contained abundant immunoreactive cathepsins K and S. Most of the elastolytic activity of tissue extracts associated with human atheroma compared to non-atherosclerotic arteries could be inhibited with E64, a non-selective cysteine protease inhibitor.

Tumor progression and metastasis are characterized by the invasion of tumors into adjacent tissues as well as by the dissociation of cancer cells from primary tumors and the infiltration of metastatic cells into organs. These processes are associated with the degragation of extracellular matrix proteins and thus require proteolytic activity. Cathepsin K has been identified in primary breast tumors, as well as in breast tumor-derived bone metastasis (Littlewood-Evans et al., *Cancer Res.* 1997, 57, 5386–5390).

Different classes of compounds, such as aldehydes, □-ketocarbonyl compounds, halomethyl ketones, diazomethyl ketones, (acyloxy)methyl ketones, ketomethylsulfonium salts, epoxy succinyl compounds, vinyl sulfones, aminoketones, and hydrazides have been identified as cysteine protease inhibitors (Schirmeister et al., *Chem. Rev.* 1997, 97, 133–171; Veber et al., *Proc. Natl. Acad. Sci. USA* 1997, 94, 14249–14254). The shortcomings these compounds suffer from include lack of selectivity, poor solubility, rapid plasma clearance and cytotoxicity. A need therefore exists for novel inhibitors useful in treating diseases caused by pathological levels of proteases, especially cysteine proteases, including cathepsins, especially cathepsin K.

SUMMARY OF THE INVENTION

The present invention relates to novel heteroaryl nitrile derivatives, their manufacture and use as medicaments. In particular, the invention relates to novel nitriles of general formula (I)

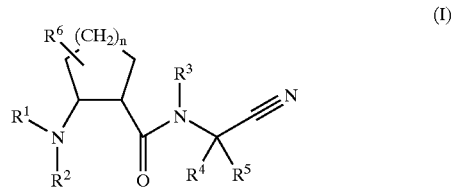

wherein
$R^1$ is heteroaryl, —$(R'R'')_mCO$—$R^a$ or $S(O)_p$—$R^a$ wherein
  R' and R'' are independently hydrogen or lower alkyl;
  m is zero or one;
  p is one or two;
  $R^a$ is heteroaryl, heteroaryl-lower-alkyl, or heteroaryl-lower-alkoxy wherein the heteroaryl in each of the preceding is selected from the group consisting of indolyl, pyridyl, quinolinyl, isoquinolinyl, N-oxo-quinolinyl, N-oxo-isoquinolinyl, naphthyridinyl, pyrazolyl, indazolyl, furo[2,3-b]pyridinyl, furo[2,3-c]pyridinyl, furo[3,2-c]pyridinyl, furo[3,2-b]pyridinyl, 1H -pyrrolo[3,2-b]pyridinyl, 1H-pyrrolo[2,3-b]pyridinyl, 1H-pyrrolo[3,2-c]pyridinyl, 1H -pyrrolo[2,3-c]pyridinyl, 1H-pyrazolo[3,4-b] pyridine, 1H-pyrazolo[3,4-c]pyridine, 1H -pyrazolo[4,3-b]pyridine, 1H-pyrazolo[4,3-c]pyridine, benzothiazolyl, azaindolyl, imidazo[2,1-b] benzothiazolyl and indolizinyl each optionally substituted;
$R^2$ is hydrogen or lower-alkyl;
$R^3$ is hydrogen or lower-alkyl;
$R^4$ is hydrogen or lower-alkyl;
$R^5$ is hydrogen, lower-alkyl, heteroalkyl, alkoxyacylalkyl, cycloalkyl, cycloalkyl-loweralkyl, aryl aralkyl, heteroaryl or heteroaryl-loweralkyl;
$R^6$ is hydrogen or lower-alkyl;
n is an integer from one to three;
and pharmaceutically acceptable salts and/or pharmaceutically acceptable esters thereof.

DETAILED DESCRIPTION OF THE INVENTION

The compounds of the present invention have an inhibitory activity on cysteine proteases, more paticulary on cysteine proteases of the papain superfamily, even more paticularly on cysteine proteases of the cathepsin family, most particularly on cathepsin K. It was surprisingly found, that this inhibiting effect on cathepsin K is selective with respect to other cathepsins. While compounds of general formula (I) very efficiently inhibit cathepsin K, the inhibition of other protease inhibitors such as cathepsin S, cathepsin L and cathepsin B is much weaker. Therefore the new compounds of general formula (I) are usefull for specifically inhibiting cathepsin K. They can accordingly be used for the treatment of disorders which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. Accordingly, the present invention relates to a method for the prophylactic and/or therapeutic treatment of diseases which are associated with cystein proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease, which method comprises administering a compound of formula (I) to a human being or an animal. The present invention also relates to pharmaceutical compositions comprising a compound of formula (I) and a pharmaceutically acceptable carrier and/or adjuvant. Furthermore, the present invention relates to the use of such compounds for the preparation of medicaments for the treatment of disorders which are associated with cystein proteases. The present invention also relates to processes for the preparation of the compounds of formula (I).

Definitions

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "alkyl" refers to a branched or straight chain monovalent saturated aliphatic hydrocarbon radical of one to eight carbon atoms.

The term "lower-alkyl" refers to a branched or straight chain monovalent alkyl radical of one to six carbon atoms, preferably one to four carbon atoms. This term is further exemplified by such radicals as methyl, ethyl, n-propyl, isopropyl, n-butyl, s-butyl, t-butyl and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

The term "cycloalkyl" refers to a monovalent carbocyclic radical of 3 to 10 carbon atom(s), preferably 3 to 6 carbon atoms.

"Alkylamino" or "Monoalkylamino" means a radical —NHR where R represents an alkyl, cycloalkyl or cycloalkyl-alkyl group as defined herein. Representative examples include, but are not limited to methylamino, ethylamino, isopropylamino, cyclohexylamino, and the like.

"Dialkylamino" means a radical —NRR' where R and R' independently represent an alkyl, cycloalkyl, or cycloalkylalkyl group as defined herein. Representative examples include, but are not limited to dimethylamino, methylethylamino, di(1-methylethyl)amino, (cyclohexyl)(methyl)amino, (cyclohexyl)(ethyl)amino, (cyclohexyl)(propyl)amino, (cyclohexylmethyl)(methyl)amino, (cyclohexylmethyl)(ethyl)amino, and the like.

The term "halo" refers to fluorine, chlorine, bromine and iodine, with fluorine, chlorine and bromine being preferred and chlorine and bromine being more preferred.

"Haloalkyl" means alkyl substituted with one or more same or different halo atoms, e.g., —CH2Cl, —CF3, —CH2CF3, —CH2CCl3, and the like.

"Heteroalkyl" means an alkyl radical as defined herein wherein one, two or three hydrogen atoms have been replaced with a substituent independently selected from the group consisting of —ORa, —NRbRc, and —S(O)nRd (where n is an integer from 0 to 2), with the understanding that the point of attachment of the heteroalkyl radical is through a carbon atom, wherein Ra is hydrogen, acyl, alkyl, cycloalkyl, or cycloalkylalkyl; Rb and Rc are independently of each other hydrogen, acyl, alkyl, cycloalkyl, or cycloalkylalkyl; when n is 0, Rd is hydrogen, alkyl, cycloalkyl, or cycloalkylalkyl, and when n is 1 or 2, Rd is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 2-dimethylamino-propyl, 3-aminopropyl, 3-amino-2-methyl-propyl, 3-dimethylamino-2-methyl-propyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one or more substituents, preferably one or two substituents, selected from alkyl, haloalkyl, hydroxyalkyl, heteroalkyl, acyl, alkylene-C(O)—XR (where X is a bond, O or NR'(where R' is hydrogen or lower-alkyl) and R is hydrogen, alkyl, alkenyl, hydroxy, alkoxy, amino, monoalkylamino or dialkylamino) acylamino, amino, monoalkylamino, dialkylamino, NR'C(O)OR" (where R' is hydrogen or alkyl and R" is alkyl or alkenyl), alkylthio, alkylsulfinyl, alkylsulfonyl, arylsulfonyl, alkylsulfonylalkyl, alkylsulfinylalkyl, —SO₂NR'R" (where R' and R" are independently hydrogen, alkyl, cycloalkyl or cycloalkyl-alkyl), NRSO₂R' (where R is hydrogen or lower alkyl, and R' is alkyl, cycloalkyl, cycloalkyl-alkyl, amino, monoalkylamino or dialkylamino), alkoxy, haloalkoxy, alkoxycarbonyl, carbamoyl, hydroxy, halo, nitro, cyano, cyanoalkyl, mercapto, methylenedioxy, ethylenedioxy, benzyloxy, pyridylalkyl, pyridylalkoxy, heterocyclylalkyl, heterocyclylalkoxy, heterocyclyloxy or optionally substituted phenyl. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, napthyridinyl, benzofuranyl, tetrahydrobenzofuranyl, isobenzofuranyl, benzothiazolyl, benzoisothiazolyl, benzotriazolyl, indolyl, isoindolyl, indazolyl, benzoxazolyl, quinolyl, tetrahydroquinolinyl, isoquinolyl, benzimidazolyl, benzisoxazolyl or benzothienyl and derivatives thereof.

"Heterocyclyl" means a saturated or unsaturated non-aromatic cyclic radical of 3 to 8 ring atoms in which one or two ring atoms are heteroatoms selected from N, N(O), O, or $S(O)_n$ (where n is an integer from 0 to 2), the remaining ring atoms being C. The heterocyclyl ring may be optionally substituted independently with one, two, or three substituents selected from alkyl, haloalkyl, heteroalkyl, halo, nitro, cyanoalkyl, hydroxy, alkoxy, amino, monoalkylamino or dialkylamino. More specifically the term heterocyclyl includes, but is not limited to, tetrahydropyranyl, piperidino, N-methylpiperidin-3-yl, piperazino, 4-methyl-piperazino, N-methylpyrrolidin-3-yl, 3-pyrrolidino, morpholino, thiomorpholino, thiomorpholino-1-oxide, thiomorpholino-1,1-dioxide, pyrrolinyl, imidazolinyl, and the derivatives thereof.

"Heterocyclylalkyl" means a group $-R^x-R^y$ where $R^x$ is an alkylene group and $R^y$ is a heterocyclyl group. Representative examples include, but are not limited to, 2-(morpholin-4-yl)ethyl, 3-(morpholin-4-yl)-propyl, 2-(4-methyl-piperazin-1-yl)ethyl, 3-(4-methyl-piperazin-1-yl)-propyl, 3-(piperidin-1-yl)propyl and the like.

"Heterocyclyl-alkoxy" means a group $-OR^x-R^y$ where $R^x$ is an alkylene group and $R^y$ is a heterocyclyl group. Representative examples include, but are not limited to 2-(morpholin-4-yl)ethoxy, 2-(4-methyl-piperazin-1-yl) ethoxy and the like.

"Heterocyclyloxy" means a group $O-R^y$ where $R^y$ is a heterocyclyl group. Representative examples include but are not limited to tetrahydropyranyloxy and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl. Accordingly, as used herein, the term "hydroxyalkyl" is used to define a subset of heteroalkyl groups.

The term "alkoxy" refers to the group R'—O—, wherein R' is an alkyl. The term "lower-alkoxy" refers to the group R'—O—, wherein R' is a lower-alkyl.

The term "alkenyl" stands for alone or in combination with other groups, a straight-chain or branched hydrocarbon residue containing an olefinic bond and up to 20, preferably up to 16 C-atoms. The term "lower-alkenyl" refers to a straight-chain or branched hydrocarbon residue containing an olefinic bond and up to 7, preferably up to 4 C-atoms.

"Aryl" means a monocyclic or bicyclic aromatic hydrocarbon radical which is optionally substituted with one or more substituents, preferably one, two or three, substituents preferably selected from the group consisting of alkyl, haloalkyl, hydroxyalkyl, heteroalkyl, acyl, acylamino, amino, alkylamino, dialkylamino, alkylthio, alkylsulfinyl, alkylsulfonyl, —SO$_2$NR'R" (where R' and R" are independently hydrogen or alkyl), alkoxy, haloalkoxy, alkoxycarbonyl, carbamoyl, hydroxy, halo, nitro, cyano, mercapto, methylenedioxy or ethylenedioxy. More specifically the term aryl includes, but is not limited to, phenyl, chlorophenyl, fluorophenyl, methoxyphenyl, 1-naphthyl, 2-naphthyl, and the derivatives thereof.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

The term "pharmaceutically acceptable esters" embraces esters of the compounds of formula (1), in which hydroxy groups have been converted to the corresponding esters with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention refers to compounds of formula (I)

wherein $R^1$ is heteroaryl, $-(CR'R'')_m CO-R^a$ or $S(O)_p-R^a$
   wherein:
   R' and R" are independently hydrogen or lower alkyl;
   m is zero or one;
   p is one or two
   n is an integer from one to three;
   $R^a$ is heteroaryl, heteroaryl-lower-alkyl, or heteroaryl-lower-alkoxy wherein the heteroaryl in each of the preceding is selected from the group consisting of indolyl, pyridyl, quinolinyl, isoquinolinyl, N-oxo-quinolinyl, N-oxo-isoquinolinyl, naphthyridinyl, pyrazolyl, indazolyl, furo[2,3-b]pyridinyl, furo[2,3-c]pyridinyl, furo[3,2-c]pyridinyl, furo[3,2-b]pyridinyl, 1H-pyrrolo[3,2-b]pyridinyl, 1H-pyrrolo[2,3-b]pyridinyl, 1H-pyrrolo[3,2-c]pyridinyl, 1H-pyrrolo[2,3-c]pyridinyl, 1H-pyrazolo[3,4-b]pyridine, 1H-pyrazolo[3,4-c]pyridine, 1H-pyrazolo[4,3-b]pyridine and 1H-pyrazolo[4,3-c]pyridine, each optionally substituted;

$R^2$ is hydrogen or lower-alkyl $R^3$ is hydrogen or lower-alkyl $R^4$ is hydrogen or lower-alkyl.

$R^5$ is hydrogen, lower-alkyl, heteroalkyl, alkoxyacylalkyl, cycloalkyl, cycloalkyl-loweralkyl, aryl aralkyl, heteroaryl or heteroaryl-loweralkyl;

$R^6$ is hydrogen or lower-alkyl;

and pharmaceutically acceptable salts and/or pharmaceutically acceptable esters thereof.

The compounds of formula (I) have at least 2 asymmetric carbon atoms and can exist in the form of optically pure enantiomers or as racemates. The invention embraces all of these forms. Preferred compounds of formula (I) are compounds of formula (Ia)

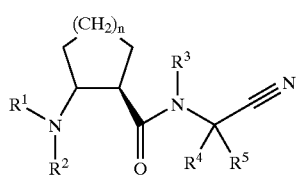

wherein $R^1$, $R^2$, $R^3$, $R^4$, $R^5$ and n have the significances given above and pharmaceutically acceptable salts and/or pharmaceutically acceptable esters thereof. The compounds of formula (Ia) encompass cis- as well as trans-compounds. Other preferred compounds of formula (I) are cis-compounds of formula (Ib)

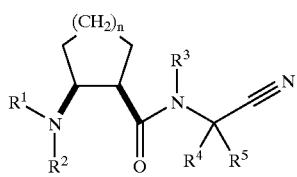

wherein $R^1$, $R^2$, $R^3$, $R^4$, $R^5$ and n have the significances given above and pharmaceutically acceptable salts and/or pharmaceutically acceptable esters thereof. Further preferred compounds of formula (I) are compounds of formula (Ic)

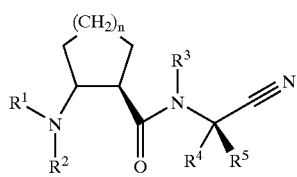

wherein $R^1$, $R^2$, $R^3$, $R^4$, $R^5$ and n have the significances given above and pharmaceutically acceptable salts and/or pharmaceutically acceptable esters thereof. The compounds of formula (Ic) encompasses cis- as well as trans-compounds.

Compounds of formula (I) in which n is 2 are preferred.

Compounds of formula (I) in which $R^2$, $R^3$, and/or $R^4$ are hydrogen are also preferred.

Also preferred are compounds where $R^4$ and $R^5$ are both hydrogen as well as compounds where $R^4$ is hydrogen and $R^5$ is cycloalkyl or alkyl, particularly cyclopropyl or isobutyl.

Compounds of Formula (I) where $R^1$ is —$(CH_2)_m CO$—$R^a$ are preferred, particularly those where m is zero and $R^a$ is indolyl, pyridyl, quinolinyl, isoquinolinyl, N-oxo-quinolinyl, N-oxo-isoquinolinyl, pyrazolyl or indazoly, each optionally substituted; more particularly optionally substituted indolyl (particularly optionally substituted 2-indolyl and 5-indolyl) and indazolyl. Other contemplated optionally substituted 2-indolyl compounds are those where $R^a$ is of the formula shown below.

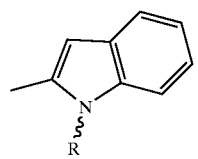

wherein R is selected from the substituents shown below.

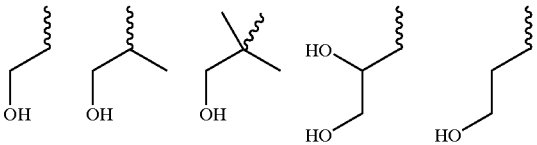

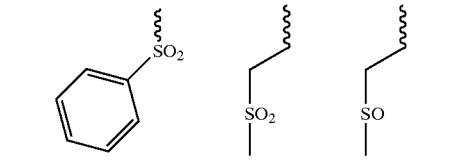

Also preferred are compounds of Formula (I) where $R^1$ is heteroaryl, particularly optionally substituted indolyl or indazolyl.

The invention also relates to the use of compounds of formula (I) as defined above for the treatment or prophylaxis of diseases which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. In a preferred embodiment, the invention relates to the use of compounds as defined above for the treatment or prophylaxis of osteoporosis, instable angina pectoris or plaque rupture.

Further, the invention relates to compounds as defined above for use as therapeutic active substances, in particular in context with diseases which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. In a preferred embodiment, the invention relates to compounds as defined above for use as therapeutic active substances, in particular in context with osteoporosis, instable angina pectoris or plaque rupture.

The invention also relates to pharmaceutical compositions comprising a compound as defined above and a pharmaceutically acceptable carrier and/or adjuvant, in particular for use in context with diseases which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. In a preferred embodiment, the invention relates to pharmaceutical compositions comprising a compound as defined above and a pharmaceutically acceptable carrier and/or adjuvant for use in context with osteoporosis, instable angina pectoris or plaque rupture.

A further embodiment of the present invention refers to the use of compounds as defined above for the preparation of medicaments for the treatment or prophylaxis of diseases which are associated with cystein proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. In a preferred embodiment, the invention relates to the use of compounds as defined above for the preparation of medicaments for the treatment or prophylaxis of osteoporosis, instable angina pectoris or plaque rupture. Such medicaments comprise a compound as defined above.

An additional embodiment of the invention relates to a method for the prophylactic and/or therapeutic treatment of disorders in which cathepsin K plays a significant pathological role, such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease, which method comprises administering a compound as defined above to a human being or an animal. A preferred embodiment of the invention relates to a method for the prophylactic and/or therapeutic treatment of osteoporosis, instable angina pectoris or plaque rupture, which method comprises administering a compound as defined above to a human being or an animal.

The invention further relates to a process for the manufacture of compounds of general formula (I) which process comprises a) reacting a compound of formula (II)

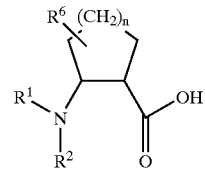

(II)

with a compound of formula (III)

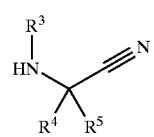

(III)

wherein $R^1$, $R^2$, $R^3$, $R^4$, $R^5$, and n have the significances given above, or b) reacting a compound of formula (IV)

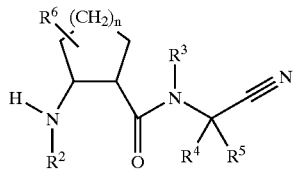

(IV)

with a compound of formula (V) or (VI)

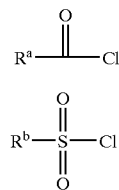

(V)

(VI)

or c) reacting a ester of Formula (VII) (where R is for example an alkyl group) with a compound $R^2CO_2H$ of Formula (VIII) to provide a compound of Formula IX which is hydrolysed and treated with a compound of Formula (X) to give the amide of Formula (XI) which is then converted to a compound of Formula (I) by treatment with a dehydrating agent. Representative, but nonlimiting dehydrating agents include trifluoroacetic anhydride, Burgess reagent, TsCl, $SOCl_2$, $COCl_2$, $P_2O_5$ and $POCl_3$.

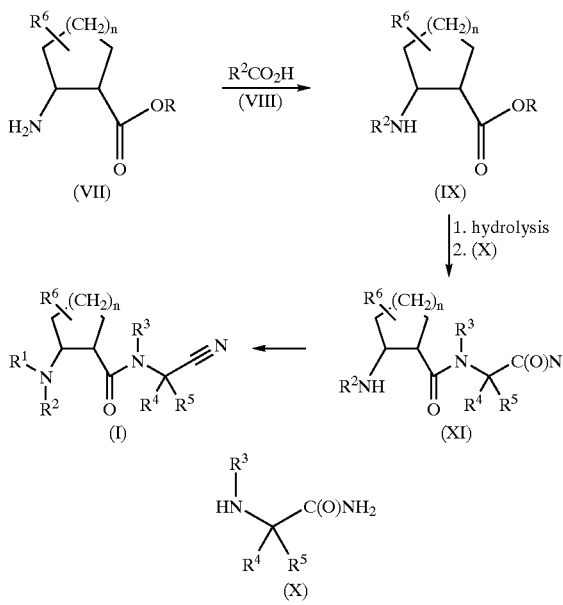

wherein $R^2$, $R^3$, $R^4$, $R^5$, $R^a$, $R^b$ and n have the significances given above.

The invention also relates to a process as described above, which process comprises the preparation of pharmaceutically acceptable salts and/or pharmaceutically acceptable esters. The formation of the esters and/or salts can be carried out at different stages of the process, e.g. with the compound of formula (I) or with the corresponding starting materials.

The reaction of a compound of formula (II) with a compound of formula (III) can be carried out by methods known to the person skilled in the art. The reaction can conveniently be carried out by dissolving compound (II), compound (III), TPTU (O-1,2-Dihydro-2-oxo-1-pyridyl)-N,N,N', N'-tetramethyluronium tetrafluoroborate) and Hünigs base (N-Ethyldiisopropylamine) in MeCN and stirring the mixture at room temperature for 6 to 16 hours. The reaction mixture can be concentrated and the product can be obtained by methods known to the person skilled in the art, e.g. by extraction and column chromatography. Alternatively, a compound of formula (II) can be dissolved in $CH_2Cl_2$ and reacted for 6 to 16 hours at room temperature with a compound of formula (III) in the presence of N-methylmorpholin, HOBT and EDCI. The product can be isolated by methods known per se, e.g. by extraction and HPLC.

The reaction of a compound of formula (IV) with a compound of formula (V) or (VI) is conveniently carried out by preparing a solution of compound (IV) in $CH_2Cl_2$ and adding a solution of compound (V) or (VI) in $CH_2Cl_2$. To this mixture, triethylamine is added and after shaking 6 to 16 hours at room temperature formic acid is added. The product can be isolated and purified by methods known per se, e.g. by evaporation of the solvent and HPLC.

In order to prepare pharmaceutically acceptable salts and/or pharmaceutically acceptable esters of compounds of formula (I), it is possible to prepare the corresponding esters and/or salts starting from the compounds of formula (I). It is also possible, to form the esters and/or salts at an earlier stage, e.g. to form the corresponding salts an/or esters of the corresponding starting materials. The methods to prepare pharmaceutically acceptable salts and/or pharmaceutically acceptable esters as defined before are known in the art.

Compounds of formula (II) are prepared by methods known to the person skilled in the art. Conveniently, the corresponding amino acid is linked to the desired substituent $R^1$ analogously to the methods described in the examples. The resulting compound (II) is isolated by methods known per se, e.g. by extraction and evaporation of the solvent.

Compounds of formula (III) can conveniently be obtained by adding a solution of the corresponding aldehyde in $CH_2Cl_2$ to a solution of $NH_4Cl$ and NaCN in $H_2O$ and MeOH at 0° C. The mixture is stirred and allowed to warm to room temperature. After addition of $NH_3$ solution and completion of the reaction the resulting compound of formula (III) is isolated and purified by methods known to the person skilled in the art, e.g. by extraction. The corresponding hydrochlorid can be prepared by methods known per se.

Chiral compounds of formula (III) can conveniently be obtained by adding ammonium bicarbonate to a mixed anhydride (prepared from a suitable t-BOC protected amino acid and di-tert-butyl dicarbonate) at 15° C. The reaction mixture is stirred at room temperature for 1–5 h. After completion of the reaction the resulting t-BOC protected amino acid amide is isolated and purified by methods known to the person skilled in the art, e.g. by extraction. The Boc protected amino acid amide and triethylamine are dissolved in THF and trifluoroacetic acid anhydride at 0° C. The mixture is stirred for 2 h at −10° C. After isolation and purification of the resulting intermediate product, e.g. by evaporation of the solvent and flash chromatography, the t-BOC protective group can be cleaved off with HCl in acetic acid to yield the desired compound of formula (III).

Compounds of formula (IV) can conveniently be obtained by reacting the corresponding t-BOC protected amino acid with a compound of formula (III) analogous to the method described above. After isolation and purification of the resulting intermediate product, e.g. by evaporation of the solvent and flash chromatography, the t-BOC protective group can be cleaved off with trifluoro-acetic acid to yield the desired compound of formula (IV) with trifluoro-acetic acid.

Compounds of formula (V) and (VI) are either commercially available or can be obtained by methods known in the art.

The present invention relates to all compounds of formula (I), as prepared by one of the processes described above.

The inhibitory activity of the compounds against cathepsin K, S, L and B was tested at room temperature in 96-wells opaque white polystyrene plates (Costar). The cathepsin K inhibitory activity was tested as follows:

5 μl of an inhibitor diluted in 5 mM sodium phosphate, NaCl 15 mM pH 7.4 containing 1% DMSO (final concentrations: 10–0.0001 μM) were preincubated for 10 min with 35 μl of human recombinant cathepsin K (final concentration: 1 mM) diluted in assay buffer (100 mM sodium acetate pH 5.5 containing 5 mM EDTA and 20 mM cysteine). After addition of 10 μl of the fluorogenic substrate Z-Leu-Arg-MCA diluted in assay buffer (final concentration: 5 μM), increase of fluorescence (excitation at 390 mM and emission at 460 mM) was measured for 7.5 min every 45 sec. The initial velocity (RFU/min) was derived from the linear fit of the 11 reading points.

The cathepsin B inhibitory activity was assayed under the same conditions as the cathepsin K inhibitory activity using human liver cathepsin B (Calbiochem) at a final concentration of 1 nM.

The cathepsin L inhibitory activity was assayed under the same conditions as the cathepsin K inhibitory activity using human liver cathepsin L (Calbiochem) at a final concentration of 3 nM.

Cathepsin S inhibitory activity was assayed analogously to the cathepsin K inhibitory activity, except that the buffer was 100 mM potassium phosphate, 5 mM EDTA, 5 mM DTT (freshly added), 0.01% Triton X-100, pH 6.5 and the fluorogenic substrate was Z-Val-Val-Arg-MCA (Bachem) (final concentration: 20 μM). Human recombinant cathepsin S (Wiederanders et al., *Eur. J. Biochem.* 1997, 250, 745–750) was used at a final concentration of 0.5 nM.

The data for inhibition of Cathepsin K for the compounds shown in Examples 1, 2, 4 5 and 11 are given below. The results are given as $IC_{50}$ values which denote the concentration of the inhibitor at which the enzymatic activity is inhibited by 50%. The $IC_{50}$ values are determined from a linear regression curve from a logit-log plot.

| Example | Cathepsin K $IC_{50}$ (μMol/l) |
| --- | --- |
| 1 | 0.018 μM |
| 2 | 0.0454 μM |
| 4 | 0.0964 μM |
| 5 | 0.0600 μM |
| 11 | 0.0030 |

Selected compounds proved to be efficacious in a nonhuman primate bone resorption model. (G. B. Stroup et al., Journal of Bone and Mineral Research, Vol. 16, Number 10, 2001 (1739–1746)). Treatment of cynomolgus monkeys with the compounds claimed resulted in a significant reduction in serum markers (NTx and CTx) of bone resorption relative to untreated controls.

It will be appreciated that the compounds of general formula (I) in this invention may be derivatised at functional groups to provide derivatives which are capable of conversion back to the parent compounds in vivo.

As mentioned earlier, medicaments containing a compound of formula (I) are also an object of the present invention, as is a process for the manufacture of such medicaments, which process comprises bringing one or more compounds of formula (I) and, if desired, one or more other therapeutically valuable substances into a galenical administration form.

The pharmaceutical compositions may be administered orally, for example in the form of tablets, coated tablets, dragées, hard or soft gelatine capsules, solutions, emulsions or suspensions. Administration can also be carried out rectally, for example using suppositories; locally or percutaneously, for example using ointments, creams, gels or solutions; or parenterally, e.g. intravenously, intramuscularly, subcutaneously, intrathecally or transdermally, using for example injectable solutions. Furthermore, administration can be carried out sublingually or as opthalmological preparations or as an aerosol, for example in the form of a spray.

For the preparation of tablets, coated tablets, dragées or hard gelatine capsules the compounds of the present invention may be admixed with pharmaceutically inert, inorganic or organic excipients. Examples of suitable excipients for tablets, dragées or hard gelatine capsules include lactose, maize starch or derivatives thereof, talc or stearic acid or salts thereof.

Suitable excipients for use with soft gelatine capsules include for example vegetable oils, waxes, fats, semi-solid or liquid polyols etc.; according to the nature of the active ingredients it may however be the case that no excipient is needed at all for soft gelatine capsules.

For the preparation of solutions and syrups, excipients which may be used include for example water, polyols, saccharose, invert sugar and glucose.

For injectable solutions, excipients which may be used include for example water, alcohols, polyols, glycerine, and vegetable oils.

For suppositories, and local or percutaneous application, excipients which may be used include for example natural or hardened oils, waxes, fats and semi-solid or liquid polyols.

The pharmaceutical compositions may also contain preserving agents, solubilising agents, stabilising agents, wetting agents, emulsifiers, sweeteners, colorants, odorants, salts for the variation of osmotic pressure, buffers, coating agents or antioxidants. As mentioned earlier, they may also contain other therapeutically valuable agents.

It is a prerequisite that all adjuvants used in the manufacture of the preparations are non-toxic.

Intravenous, intramuscular or oral administration is a preferred form of use. The dosages in which the compounds of formula (I) are administered in effective amounts depend on the nature of the specific active ingredient, the age and the requirements of the patient and the mode of application. In general, daily dosages of about 1 mg–1000 mg, preferably 5 mg–500 mg, per day come into consideration.

The following Examples shall illustrate preferred embodiments of the present invention but are not intended to limit the scope of the invention.

The corresponding starting materials are either commercially available or can be obtained by methods known in the art (e.g. from: DE 26 24 290; WO 98/0354; Chem. Pharm. Bull., 38(2), 350–354 (1990), Chiral Synthon Obtained with Pig Liver Esterase: Introduction of Chiral Centers into Cyclohexene Skeleton; J. Chem. Soc. Perkin Trans., 1, 1411–1415 (1994), Asymmetric Synthesis of (−)-(1R,2S)-Cispentacin and Related cis- and trans-2-Amino Cyclopentane- and Cyclohexane-1-carboxylic Acids) or can be obtained by methods analogous to the methods described before.

| | Abbreviations/Acronyms |
| --- | --- |
| Burgess Reagent | (Methoxycarbonylsulfamoyl)triethylammonium hydroxide, inner salt |
| DCM, CH2Cl2 | Dichloromethane |
| DIC | 2-Dimethylaminoisopropyl chloride hydrochloride |
| DIPEA | N,N-Diisopropylethylamine |
| DMAP | 4-Dimethylaminopyridine |
| DMF | N,N-Dimethylformamide |
| EDCl | 1-(3-Dimethylaminopropyl)-3-ethylcarbodiimide hydrochloride |
| HOBT | 1-Hydroxybenzotriazole hydrate |
| MEOH | Methanol |
| NMM | N-Methylmorpholine |
| NMP | 1-Methyl-2-pyrrolidinone |
| TBS | tert-Butyldimethylsilyl protecting group |
| TFA | Trifluoroacetic acid |
| THF | Tetrahydrofuran |

EXAMPLE 1

Example of Method A in Tables

Synthesis of N-[(1S,2R)-2-({[cyano(cyclopropyl)methyl]amino}carbonyl)cyclohexyl]-1H-indole-2-carboxamide

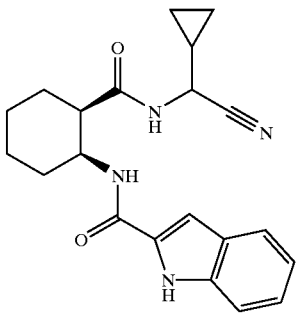

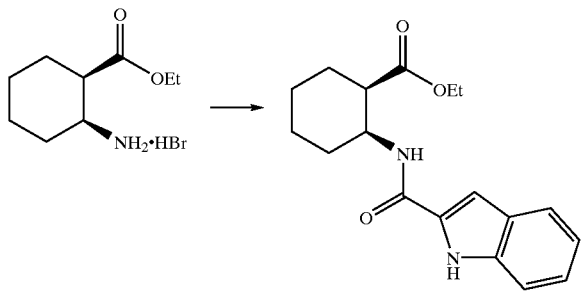

To 300 mg (1.19 mmol) of ethyl (1R,2S)-2-aminocyclohexanecarboxylate HBr salt (Xu, Daquiang et al., *Tetrahedron:Asymmetry* (1988), 9(10) 1635) dissolved in 8 mL DMF was added 192 mg (1.19 mmol) of indole-2-carboxylic acid, 228 mg (1.19 mmol) of EDCI, 161 mg (1.19 mmol) of HOBT and 0.458 mL (4.16 mmol) of N-methylmorpholine. The reaction mixture was stirred at room temperature overnight, partitioned between ethyl acetate and water, dried over magnesium sulfate and concentrated to provide ethyl (1R,2S)-2-[(1H-indol-2-ylcarbonyl)amino]cyclohexane-carboxylate.

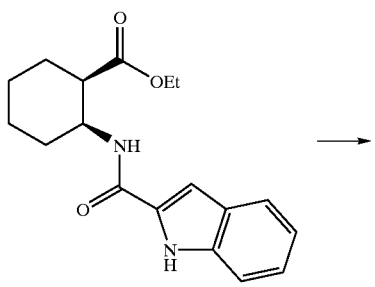

-continued

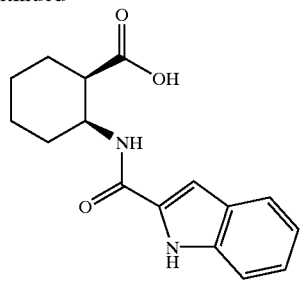

The crude reaction mixture was dissolved in 8 mL methanol, and 110 mg (2.62 mmol) of lithium hydroxide dissolved in 2 mL water was added. The reaction mixture was stirred overnight, partitioned between dichloromethane and 1 N HCl, dried over magnesium sulfate and concentrated to provide 220 mg of (1R,2S)-2-[(1H-indol-2-ylcarbonyl)amino]cyclohexanecarboxylic acid [educt 1], pure by $^1$H NMR. (66% over two steps).

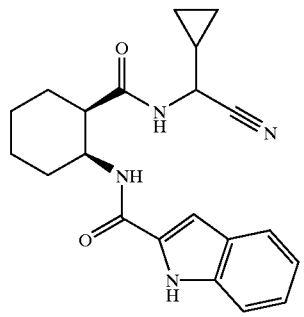

To 110 mg (0.38 mmol) of the acid above dissolved in 2 mL DMF was added 50 mg (0.38 mmol) R, S-amino(cyclopropyl)acetonitrile [educt 2], 73 mg (0.38 mmol) of EDCI, 51 mg (0.38 mmol) of HOBT and 0.146 mL (1.33 mmol) of N-methylmorpholine. The reaction mixture was stirred at room temperature overnight, partitioned between ethyl acetate and water, dried over magnesium sulfate and concentrated. Column chromatography, eluting with 10% acetone in dichloromethane, provided 67 mg of the title compound N-[(1S,2R)-2-({[cyano(cyclopropyl)methyl]amino}carbonyl)cyclohexyl]-1H-indole-2-carboxamide, 93% pure by HPLC. (48%)

EXAMPLE 2

Example of Method B-1 in Tables

Synthesis of N-[(1S,2R)-2-({[(1S)-1-cyano-2-phenylethyl]amino}carbonyl)cyclohexyl]quinoline-2-carboxamide

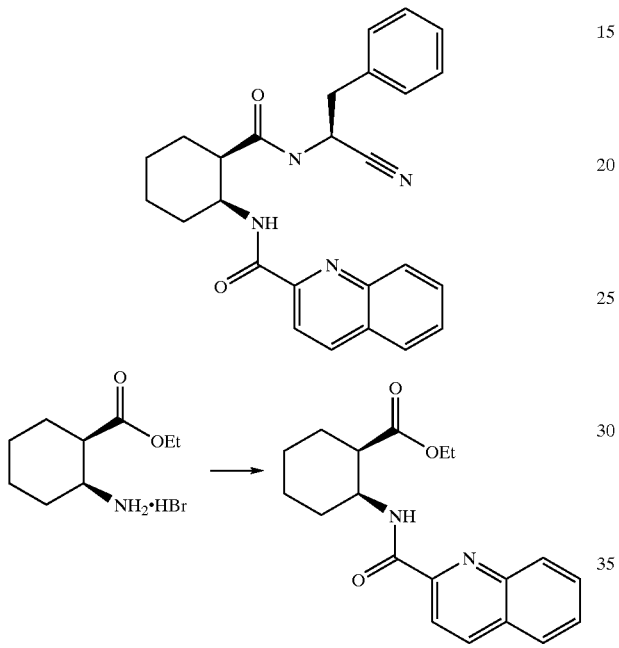

To 190 mg (0.75 mmol) of ethyl (1R,2S)-2-aminocyclohexanecarboxylate HBr salt dissolved in 5 ml DMF was added 140 mg (0.80 mmol) of quinaldic acid, 152 mg (0.79 mmol) of EDCI, 108 mg (0.80 mmol) of HOBT and 0.26 ml (2.37 mmol) of N-methylmorpholine. The reaction mixture was stirred at room temperature overnight, partitioned between ethyl acetate and water, dried over magnesium sulfate and concentrated to provide 290 mg of ethyl (1R,2S) -2-[(1H-quino-2-ylcarbonyl)amino]cyclohexanecarboxylate (crude).

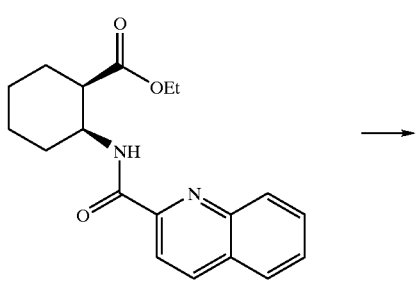

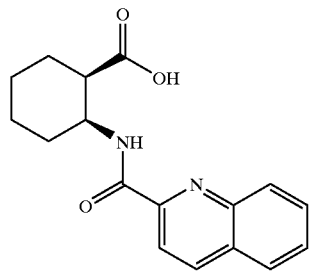

The crude reaction material above was dissolved in 8 ml THF, and 120 mg (2.86 mmol) of lithium hydroxide dissolved in 2 ml water was added. The reaction mixture was heated to 60° C. and stirred for overnight, partitioned between dichloromethane and 1 N HCl, dried over magnesium sulfate and concentrated to provide 260 mg of (1R, 2S)-2-[(1H-quino-2-ylcarbonyl)amino] cyclohexanecarboxylic acid [educt 1].

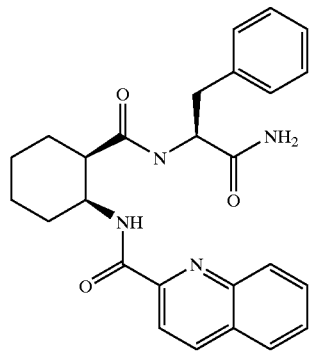

To 260 mg (0.87 mmol) of the acid above dissolved in 5 ml DMF was added 140 mg (0.85 mmol) L-phenylalaninamide [educt 2], 120 mg (0.88 mmol) of HOBT, 170 mg (0.88 mmol) of EDCI and 0.34 ml (3.06 mmol) of N-methylmorpholine. The reaction mixture was stirred at room temperature overnight, partitioned between ethyl acetate and water, dried over magnesium sulfate and concentrated to give the 388 mg of the crude product as a white solid.

19

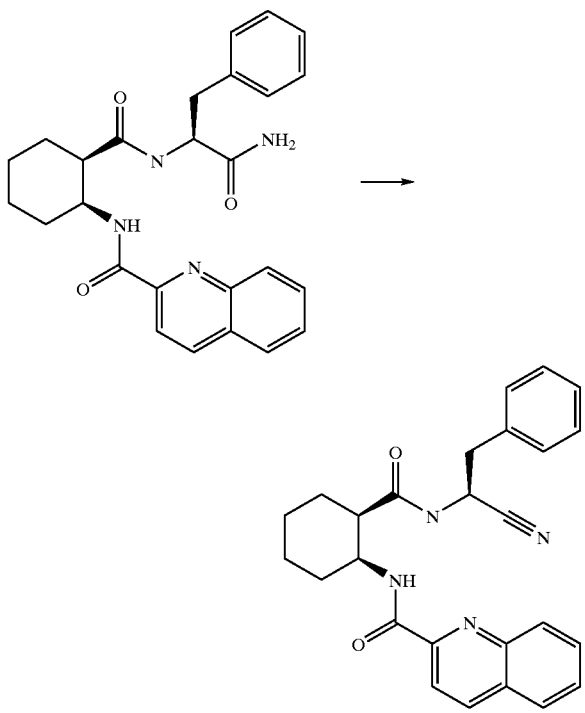

To the solution of 388 mg (0.87 mmol) of the crude product from above in dichloromethane (10 ml) was added Burgess Reagent 210 mg (0.88 mmol). The mixture was stirred at room temperature for overnight. After the dichloromethane was removed, the residue was dissolved in 2 ml MeOH and purified with preparative thin layer chromatography (hexane: ethyl acetate 1:1) to give the product as a white foam: 88 mg (0.21 mmol). 27.5% yield.

EXAMPLE 3

Example of Method B-2 in Tables

Synthesis of N-[(1S,2R)-2-({[(S)-cyano(cyclopropyl)methyl]amino}carbonyl)cyclohexyl]-1-methyl-1H-indole-2-carboxamide

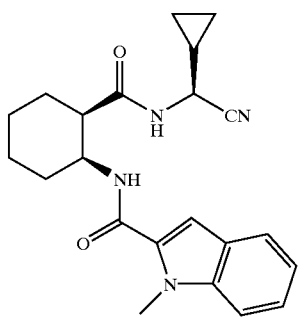

This example illustrates the preparation of N-[(1S,2R)-2-({[(S)-cyano(cyclopropyl)methyl]amino}carbonyl)cyclohexyl]-1-methyl-1H-indole-2-carboxamide starting with ethyl cis-2-amino-1-cyclohexanecarboxylate and (S)-cyclopropylglycinamide or alternatively with ethyl cis-2-amino-1-cyclohexanecarboxylate and (S)-cyclopropylglycine nitrile.

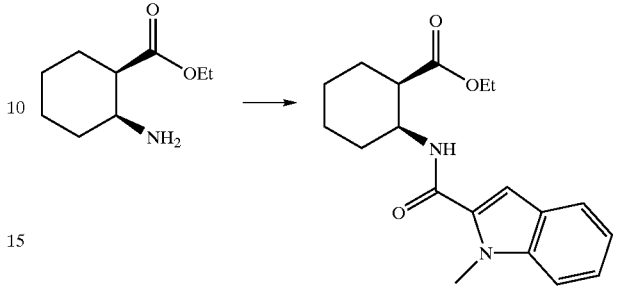

To a 0° C. solution of ethyl cis-2-amino-1-cyclohexanecarboxylate HBr salt (9.03 g, 35.8 mmol), 1-methylindole-2-carboxylic acid (6.18 g, 35.3 mmol), HOBT (5.45 g, 40.3 mmol), and EDCI*HCl (7.45 g, 38.9 mmol) in 70 mL of anhydrous DMF was added N-methylmorpholine(7.8 mL, 71 mmol). The reaction mixture was stirred for 24 h at room temperature. The reaction mixture was cooled in an ice bath and treated with 140 mL of water. 140 mL of ethyl acetate was added to the resulting yellow suspension and stirred until the solids dissolved. An additional 140 mL of ethyl acetate was added and the organic layer was separated. The organic layer was washed with two 280 mL portions of 0.5 M HCl, 280 mL of brine, then dried over sodium sulfate, filtered and concentrated to give a crude yellow solid. Purification by column chromatography (30:70, ethyl acetate:hexanes) gave 10.9 g of the product as a pale green-tinted solid. Yield: 90%, MS: 329 (M+H$^+$), mp=98.1–99.0° C.

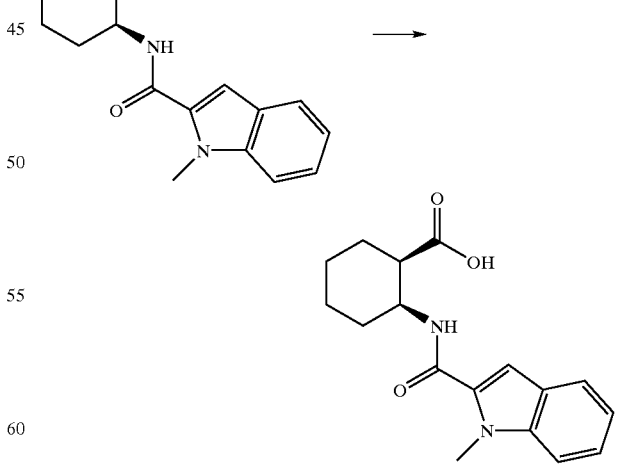

To a 0° C. solution of the ester (10.9 g, 31.8 mmol) in 100 mL of THF was added a solution of lithium hydroxide hydrate (5.29 g, 126 mmol) in 100 mL of water. The reaction mixture stirred at room temperature for 16 hours, then slowly poured into a flask containing 150 mL of a 1M HCl solution and extracted the resulting suspension with 200 mL of ethyl acetate. The organic layer was separated and washed with 200 mL of brine, dried over sodium sulfate, filtered and concentrated to give 9.49 g of the product as a white solid. Yield: 100%, MS: 301 (M+H⁺), mp=196.0–198.9° C.

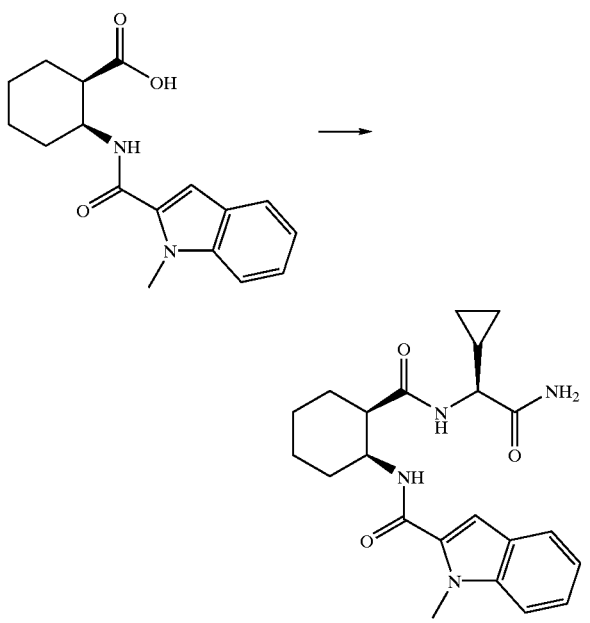

To a 0° C. solution of the carboxylic acid [educt 1](10.23 g, 34.1 mmol), (S)-cyclopropylglycinamide [educt 2](4.08 g, 35.7 mmol), HOBT (6.90 g, 51.1 mmol), and EDCI HCl (9.79 g, 51.1 mmol) in 60 mL of anhydrous DMF was added N-methylmorpholine (3.7 mL, 37 mmol). The reaction mixture was allowed to warm to room temperature and stirred for 24 hours. The reaction mixture was cooled in an ice bath and treated with 100 mL of water. The suspension was stirred for 1 hour. The precipitate was filtered and washed with copious amounts of 1M HCl followed by copious amounts of water. The precipitate was dried in vacuo to give a crude off-white solid. Purification by silica gel column chromatography (30:70, ethyl acetate:hexanes) gave 2.00 g of the amide as a white solid. Yield: 84%, MS: 397 (M+H⁺), mp=242.5–245.6° C.

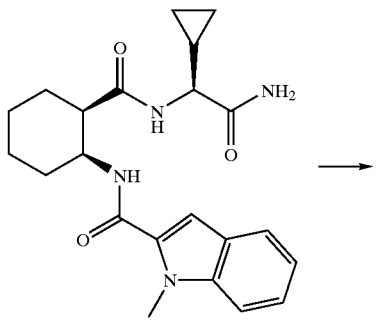

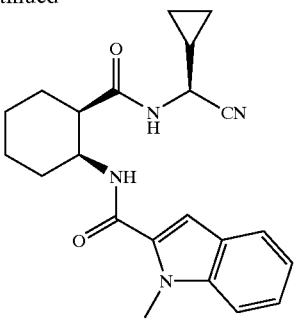

To a 0° C. solution of the amide (10.0 g, 25.2 mmol) and anhydrous pyridine (200 mL) was added trifluoroacetic anhydride (5.34 ml, 37.8 mmol) dropwise. The reaction mixture was stirred for 15 mins. at 0° C., then 250 mL of 1M aqueous HCl was added slowly. Ethyl acetate (200 mL) was added and the aqueous layer was discarded. Another 200 mL of ethyl acetate was added and the organic layer was washed with 1M aqueous HCl until the aqueous layer remained acidic. The organic layer was then washed with three portions of water, one portion of brine, dried with sodium sulfate, and concentrated to give 9.80 g of a crude solid. Initial purification by column chromatography (30:70, ethyl acetate:hexanes) gave the product (5.68 g, 59%) as an off-white solid. Recrystallization (83:17, diethyl ether:chloroform) gave 4.63 g of the product as a white solid. Yield: 48%, MS: 379 (M+H⁺), mp=166.0–168.5° C.

Alternative Synthesis

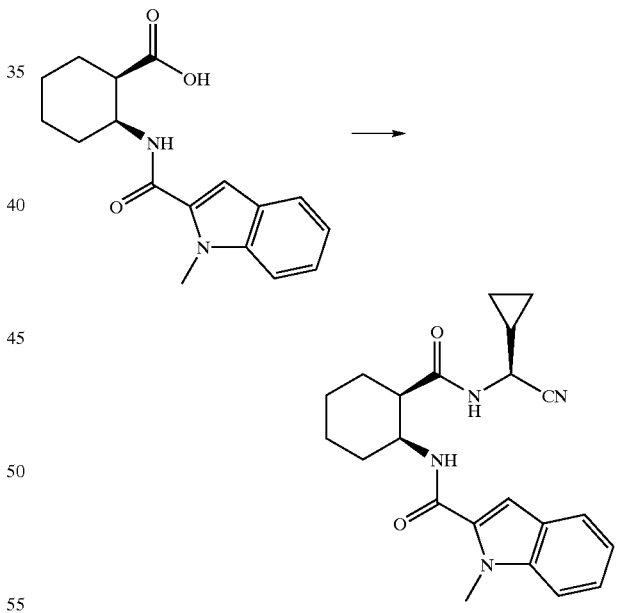

To a solution of the carboxylic acid [educt 1](514 mg, 1.71 mmol), (S)-cyclopropylglycine nitrile [educt 2](300 mg, 2.26 mmol), HOBT (255 mg, 1.89 mmol) and EDCI hydrochloride (366 mg, 1.91 mmol) in anhydrous DMF (8.0 mL) was added N-methylmorpholine (0.80 mL, 7.3 mmol). The reaction mixture was stirred at room temperature for 4 h, then 40 mL of water was added and extracted with 40 mL of ethyl acetate. The organic layer was washed with two 40 mL portions of 1M HCl and 40 mL of brine, dried over sodium sulfate, filtered and concentrated to give a crude white foam. Purification by column chromatography (40–50:60–50, ethyl acetate:hexanes) gave the product (341 mg, 53%) as a white solid as an 83:17 (S:R ratio at the glycine stereocenter, as determined by $^1$H NMR spectroscopy) mixture of diastereomers.

Synthesis of (S)-cyclopropylglycine amide [educt 2]

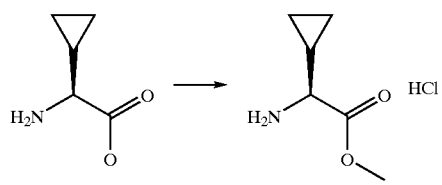

To a 0° C. solution of thionyl chloride (7.6 mL, 104 mmol) in anhydrous methanol (750 mL) was added (S)-cyclopropylglycine (10.0 g, 86.9 mmol, Eastman Chemical Company, Kingsport, Tenn.). The reaction mixture was allowed to warm to room temperature and then refluxed for 4 hrs, then cooled to room temperature and concentrated in vacuo to give a crude solid. The solids were washed with acetone to give 8.94 g of the product as a white solid. Yield: 62%, MS: 130 (M+H$^+$), mp=134.0–135.9° C.

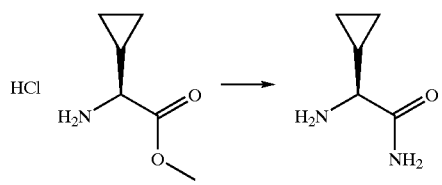

To a 0° C. solution of ammonia in methanol (100 mL, 7M) in a bomb was added (S)-cyclopropylglycine ethyl ester HCl (5.04 g, 30.4 mmol). The bomb was sealed and placed in a 70° C. oil bath for two days. The reaction mixture was cooled to room temperature and concentrated until a suspension formed. The suspension was filtered and the collected solids were washed with methanol:acetone (1:1). Another crop of solids was obtained from the mother liquor in this manner, and the combined solids were dried to give 3.52 g of the product as a white powder.

Yield: 100%, MS: 115 (M+H$^+$), mp=225.0–231.0° C., $[\alpha]_D^{25}$=+63.0 (1.00, 1M HCl).

Synthesis of (S)-cyclopropylglycine nitrile

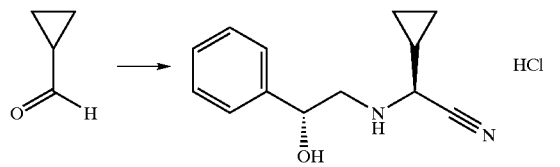

To a solution of cyclopropylcarboxaldehyde (10.27 g, 146.5 mmol) in 500 mL of anhydrous methylene chloride was added (R)-phenylglycinol (20.06 g, 146.2 mmol). The reaction mixture was stirred at room temperature for 2 h, then cooled to –26° C. with a dry ice/acetone bath. Trimethylsilyl cyanide (39.0 mL, 292 mmol) was slowly added via syringe keeping the reaction temperature below –23° C. The reaction mixture was allowed to warm to room temperature and stirred overnight. 100 mL of methanol and 150 mL of 1M HCl were added and the reaction mixture was stirred for 1 h. The reaction mixture was neutralized with 150 mL of 1M sodium hydroxide, the organic layer separated and washed with 400 mL of water, dried over sodium sulfate, filtered and concentrated to give a yellow liquid. The product was isolated as the monohydrochloride salt by treating the free amine in methylene chloride with 1M HCl in ether to give 34.24 g of a white solid as an 83:17 (S:R ratio at the glycine stereocenter, as determined by $^1$H NMR spectroscopy) mixture of diastereomers. Yield: 93%, MS: 217 (M+H$^+$), mp=106.0–108.1° C.

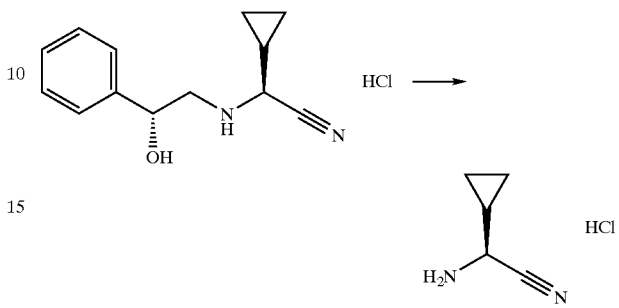

To a 0° C. solution of the glycinol adduct (5.00 g, 19.8 mmol) in 70 mL of methanol and 35 mL of methylene chloride was added lead tetracetate (9.15 g, 20.6 mmol) portionwise over a 1 minute period. The reaction mixture was stirred for 30 minutes at 0° C. and the resulting suspension was filtered through a pad of celite. The collected solids were washed with 2×100 mL of methylene chloride and the organic layer was separated, washed with 200 mL of water, dried over sodium sulfate, filtered and concentrated to the imine (3.55 g, 97%) as a clear liquid. The imine was directly hydrolyzed to give cyclopropylglycine nitrile by dissolving in ether and treating with 1M HCl in an ice bath. The hydrolysis was followed by TLC by monitoring for the disappearance of the imine (Rf=0.43, 10:90 EtOAc:hexanes). After complete hydrolysis, the aqueous layer was separated, washed with ether, then carefully concentrated on the rotary evaporator (30–42° C. water bath) and concentrated in vacuo to give the product as a hygroscopic white solid.

EXAMPLE 4

Example of Method B-3 in Tables

Synthesis of N-[(1S,2R)-2-({[(1R)-1-cyano-2-hydroxyethyl]amino}carbonyl)cyclohexyl]-1-methyl-1H-indole-2-carboxamide

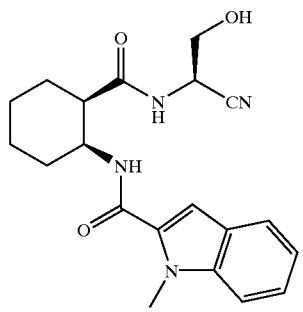

This example illustrates the preparation of N-[(1S,2R)-2-({[(1R)-1-cyano-2-hydroxyethyl]amino}carbonyl) cyclohexyl]-1-methyl-1H-indole-2-carboxamide starting with the amide, 4a, made following a procedure analogous to Example 2.

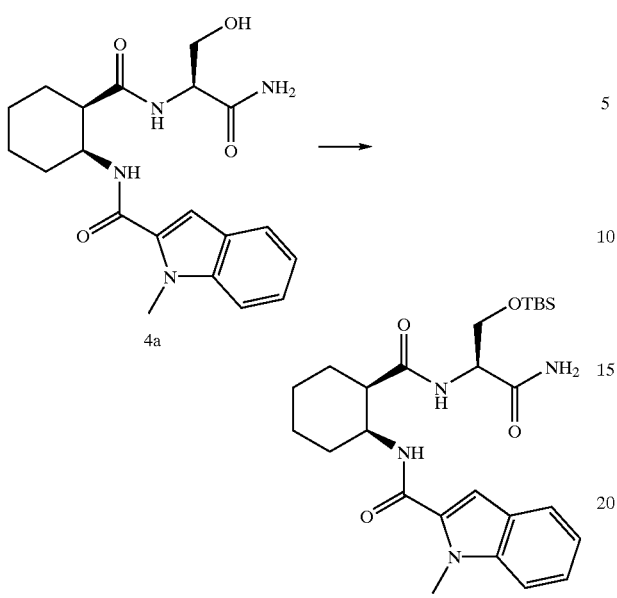

To a solution of the hydroxy amide (231 mg, 0.598 mmol) in anhydrous DMF (4 mL) were added tert-butyldimethylsilyl chloride (178 mg, 1.18 mmol) and imidazole (87 mg, 1.28 mmol). The reaction mixture was stirred at room temp for 16 h. Water (20 mL) and ethyl acetate (20 mL) were added and the aqueous layer was discarded. The organic layer was washed with two portions of water, dried with sodium sulfate, and concentrated to give a crude liquid. Purification by column chromatography (5:95, methanol:dichloromethane) gave 250 mg of the product as a clear liquid. Yield: 83%.

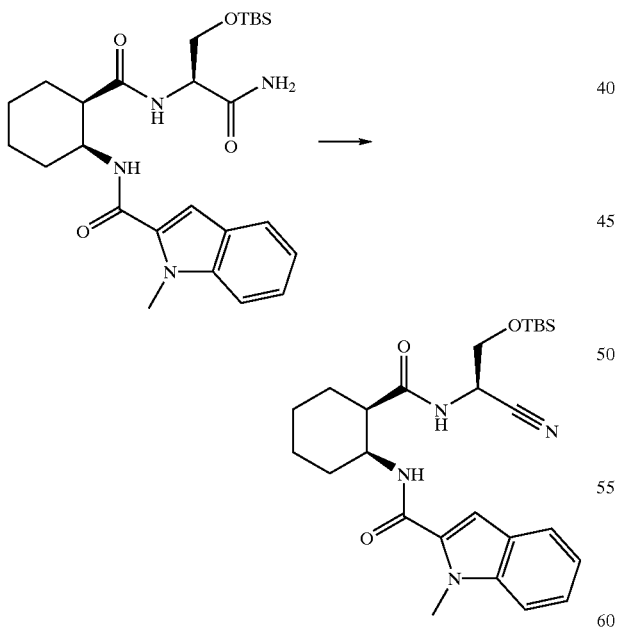

To a 0° C. solution of the amide (0.25 g, 0.50 mmol) in anhydrous pyridine (6 mL) was added trifluoroacetic anhydride (0.20 mL, 1.4 mmol) dropwise. The resulting yellow reaction mixture was stirred at 0° C. for 10 min, then 20 ml of 1M HCl solution was added. To the resulting milky suspension was added 25 mL of ethyl acetate and the aqueous layer was discarded. The organic layer was washed with two 20 mL portions of 1M HCl and 20 mL of brine, dried over sodium sulfate, filtered and concentrated to give a yellow liquid. Purification by column chromatography (20–40:80–60, ethyl acetate:hexanes) gave 127 mg of the product as a white foam solid. Yield: 53%, MS: 483.3 (M+H$^+$).

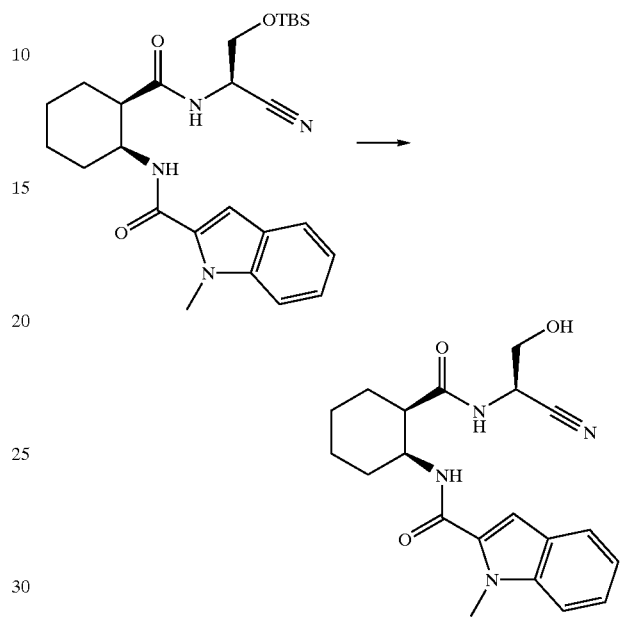

To a 0° C. solution of the TBS-ether (117 mg, 0.242 mmol) in 6 mL of anhydrous THF was added a 1M solution of tert-butylammonium fluoride (0.30 mL, 0.30 mmol) in THF. The reaction mixture was warmed to room temp, concentrated in vacuo and purified by column chromatography (5:95, methanol:dichloromethane) to give 86 mg of the product as a white foam solid. Yield: 96%, MS: 369 (M+H$^+$), mp=78.4–79.0° C.

EXAMPLE 5

Example of Method C in Tables

Synthesis of N-[2-({[(1S)-1-cyano-2-(4-nitrophenyl)ethyl]amino}carbonyl)cyclohexyl]quinoline-2-carboxamide trifluoroacetate

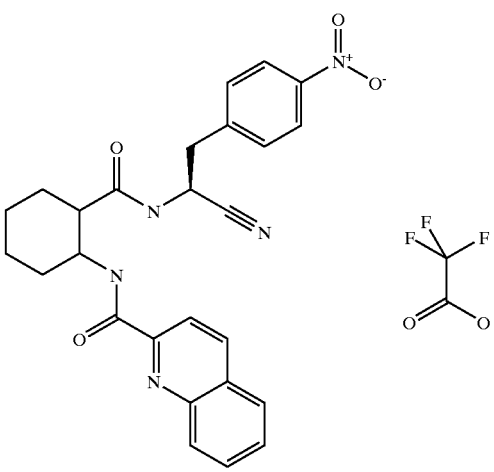

To 5.033 g of 9H-fluoren-9-ylmethoxy-2,4-dimethoxyphenyl(4-hydroxybenzyl) carbamate Rink polystyrene resin in a large glass bubbler was added 20% piperidine/DMF (80 mL). The reaction was bubbled with nitrogen for 30 minutes, filtered, and washed three times with 80 mL of CH$_2$Cl$_2$, once with MeOH and again with CH$_2$Cl$_2$. To the resin was added 3 eq DIC (1.4 mL), 0.05 eq. DMAP (1.3 mL of a 0.116 M soln in THF), 3 eq. N-[(9H-fluoren-9-ylmethoxy)carbonyl]-4-nitrophenylalanine (3.9 gr). The resin was then suspended in CH$_2$Cl$_2$ (80 mL) and bubbled with nitrogen overnight. The reaction was filtered and washed 3 times with 80 mL with CH$_2$Cl$_2$ then with MeOH and again with CH$_2$Cl$_2$. To the resin was added 80 mL of 20% piperidine/DMF. The reaction was bubbled with nitrogen for 30 min, filtered and washed three times with 80 mL of CH$_2$Cl$_2$, then with MeOH and again with CH$_2$Cl$_2$. To the resin was added 3 eq EDCI (1.7 gr), 1 eq. HOBt (0.41 gr), and 3 eq. (1R,2S)-2-{[{2-[(1Z)-prop-1-enyl]-3-vinyl-1H-inden-1-yl}methoxy)carbonyl]amino}cyclohexanecarboxylic acid (3.3 gr). The resin was then suspended in NMP (80 mL) and bubbled overnight. The reaction was then filtered and washed three times with 80 mL of CH$_2$Cl$_2$, once with MeOH and again with CH$_2$Cl$_2$ and allowed to dry in a vacuum dessicator.

To 250 mg of this resin in a solid phase extraction vial was added 20% piperidine/DMF (2.5 mL). The reaction was allowed to sit for 30 minutes, filtered and washed three times with 4 mL with CH$_2$Cl$_2$, once with MeOH and again with CH$_2$Cl$_2$. To the resin was added 3 eq DIC (56 uL), 0.05 eq. DMAP (52 uL of a 0.116 M soln in THF), 3 eq. quinaldic acid (62.3 mg). The resin was then suspended in CH$_2$Cl$_2$ (2.5 mL) and rotated overnight. The reaction was then filtered and washed three times with 4 mL of CH$_2$Cl$_2$, once with MeOH and again with CH$_2$Cl$_2$. The resin was then treated with 10% TFA/CH$_2$Cl$_2$ (2.5 ml) for 30 min, filtered and washed twice with 2.5 mL of CH$_2$Cl$_2$. The filtrate was evaporated on a Speed-Vac and dissolved in CH$_2$Cl$_2$ (2.5 mL). Burgess reagent (2 eq, 57 mg) was added and the reaction stirred overnight. The reaction was then evaporated on a Speed-Vac and purified by reverse phase high pressure liquid chromatography to yield 1.8 mg of a 95% pure sample.

EXAMPLE 6

Example of Method D in Tables

Synthesis of N-(cyanomethyl)-2-(quinolin-8-ylamino)cyclohexanecarboxamide

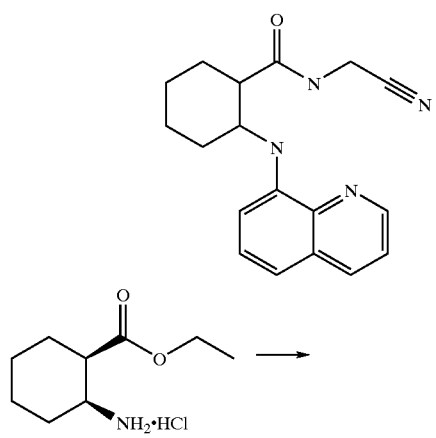

-continued

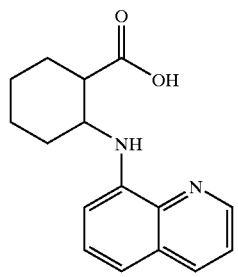

To an oven-dried Schlenk flask that was evacuated and backfilled with argon was added 726 mg (3.68 mmol) of ethyl cis-2-amino-1-cyclohexanecarboxylate HCl salt, 56 mg (0.06 mmol, 2 mol % Pd) of Pd$_2$(dba)$_3$, 77 mg (0.12 mmol, 4 mol %) of rac-BINAP, 881 mg (9.17 mmol) of sodium tert-butoxide, 500 mg (3.06 mmol) of 8-chloroquinoline, and 7.5 mL of toluene. The flask was sealed with a glass stopper and an argon balloon replacing the source. The reaction mixture was then heated to 90° C. and stirred at that temperature for 17 hours. The mixture was allowed to cool to room temperature, taken up in diethyl ether (35 mL), washed three times with saturated brine (30 mL), dried over magnesium sulfate, and concentrated to provide the crude reaction mixture. The crude mixture was re-dissolved in ethyl acetate, partitioned between ethyl acetate and 1N HCl, dried over magnesium sulfate and concentrated to provide 125 mg (15%) of 2-(quinolin-8-ylamino)cyclohexanecarboxylic acid with both cis and trans isomers in 1:1 ratio. Confirmed by $^1$H NMR.

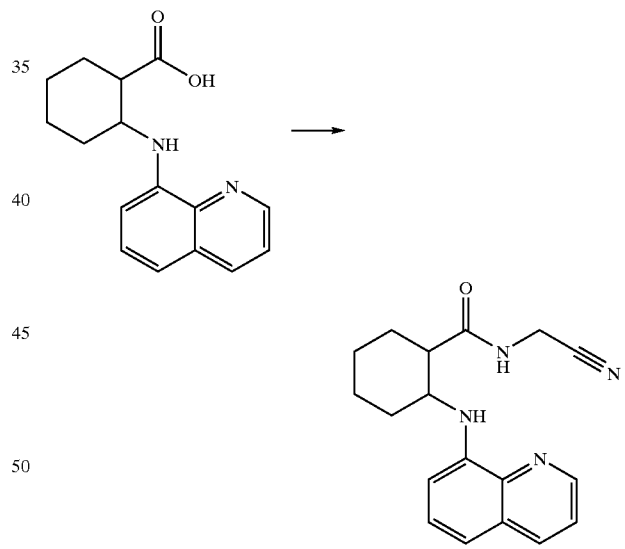

To 50 mg (0.19 mmol) of the acid above dissolved in 1.3 mL of DMF was added 18 mg (0.19 mmol) of aminoacetonitrile HCl salt, 37 mg (0.19 mmol) of EDCI, 26 mg (0.19 mmol) of HOBT, and 0.09 mL (0.78 mmol) of N-methylmorpholine. The reaction mixture was stirred at room temperature overnight, partitioned between ethyl acetate and water, dried over magnesium sulfate and concentrated. Column chromatography, eluting with solvent system hexane:ethyl acetate (7:3), and then with solvent system hexane:ethyl acetate (1:1), provided 15 mg (25%) of the corresponding cis/trans product mixture, which is the title compound of N-(cyanomethyl)-2-(quinolin-8-ylamino)cyclohexanecarboxamide, 99% pure by HPLC.

EXAMPLE 7

N-((1S,2R)-2-{[(cyanomethyl)amino]carbonyl}cyclohexyl)-6-[2-(4-methylpiperazin-1-yl)ethoxy]-1H-indole-2-carboxamide

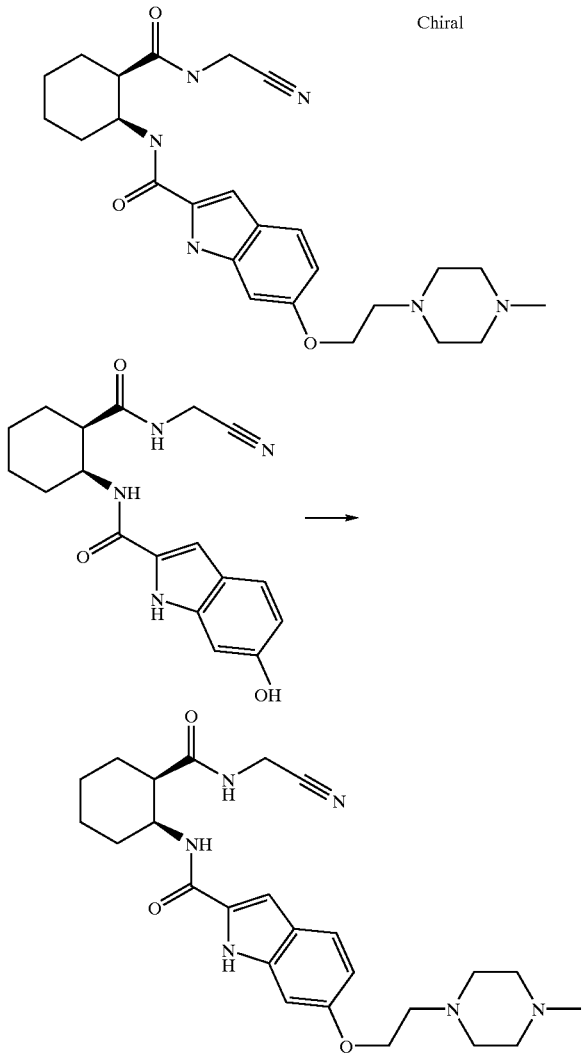

To 85 mg (0.25 mM) 6-Hydroxy-1H-indole-2-carboxylic acid [2-(cyanomethyl-carbamoyl)-cyclohexyl]-amide in 5 ml dichloromethane at 0° C. was added 144 mg (1 mM) 2-(4-Methyl-piperazin-1-yl)-ethanol, 262 mg (1 mM) triphenylphosphine and 131 mg (0.75 mM) DEAD. After several hours the mixture was allowed to warm to room temperature and stir overnight. The reaction mixture was purified directly on a preparative TLC plate and eluted with 10% methanol/dichloromethane. The product was then partitioned between 1 M HCl and ethyl acetate, the aqueous layer was neutralized and extracted with ethyl acetate, dried over magnesium sulfate and stripped to give 18.9 mg 6-[2-(4-Methylpiperazin-1-yl)-ethoxy]-1H-indole-2-carboxylic acid [2-(cyanomethyl-carbamoyl)-cyclohexyl]-amide.

Similarly were prepared:

N-((1S,2R)-2-{[(cyanomethyl)amino]carbonyl}cyclohexyl)-1-methyl-6-(2-morpholin-4-ylethoxy)-1H-indole-2-carboxamide using Mitsunobu coupling with 2-Morpholin-4-yl-ethanol.

N-((1S,2R)-2-{[(cyanomethyl)amino]carbonyl}cyclohexyl)-6-(2-morpholin-4-ylethoxy)-1H-indole-2-carboxamide using Mitsunobu coupling with 2-morpholin-4-yl-ethanol.

EXAMPLE 8

Synthesis of allyl 2-({[(1S,2R)-2-({[(S)-cyano(cyclopropyl)methyl]amino}carbonyl)cyclohexyl]amino}carbonyl)-1H-indol-6-ylcarbamate

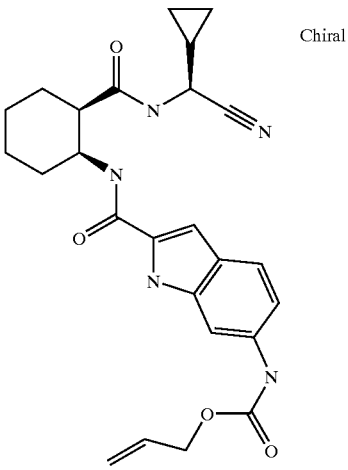

To 2.0 g (8.96 mmol) of 4-aminobenzylalcohol dissolved in 25 mL of dichloromethane and 1.81 mL (2.5 eq., 22.4 mmol) of pyridine at 0° C. was added 950 □L (8.96 mmol) of allyl chloroformate. The mixture was stirred at 0° C. for 1 h, partitioned between dichloromethane and water, dried over magnesium sulfate and concentrated. The product was purified using column chromatography, eluting with 40% ethyl acetate/hexane, to provide 2.154 g allyloxycarbonyl-protected 4-aminobenzyl alcohol, as a colorless oil.

To 2.154 g (10.39 mmol) of the above compound dissolved in 40 mL dichloromethane at 0° C. was added 4.41 g (10.39 mmol) Dess-Martin periodinane. The mixture was stirred at 0° C. for 1 h, partitioned between dichloromethane and water, dried over magnesium sulfate and concentrated. The product was purified using column chromatography, eluting with 40% ethyl acetate/hexane, to provide 1.726 g of 2 (allyl 4-formylphenylcarbamate), as a colorless oil.

To a solution of 689 mg (10.13 mmol) sodium ethoxide in 5 mL absolute ethanol at 0° C. was added a solution of 500 mg (2.44 mmol) of 2 and 1.25 g (9.75 mmol) ethylazidoacetate dissolved in 5 mL absolute ethanol and 1 mL tetrahydrofuran dropwise over 5 minutes. The mixture was stirred at 0° C. for 1.5 h, then partitioned between ethyl acetate and 1 N HCl until neutral. The organic phase was dried over magnesium sulfate, concentrated and purified by column chromatography, eluting with 25% ethyl acetate/hexane to provide 385 mg of 3 (ethyl (2E)-3-(4-{[(allyloxy)carbonyl]amino}phenyl)-2-azidoprop-2-enoate) as a yellow solid.

385 mg (1.217 mmol) of 3 was dissolved in 25 mL toluene (~0.05M solution). The mixture was heated to 80° C. for 2 h, cooled, and concentrated. Purification by column chromatography, eluting with 25% ethyl acetate/hexane provided 134 mg of 4 (ethyl 6-{[(allyloxy)carbonyl]amino}-1H-indole-2-carboxylate) as a yellow solid.

To 134 mg (0.465 mmol) of 4 dissolved in 5 mL methanol was added 43 mg (1.023 mmol) lithium hydroxide dissolved in 1 mL water. The mixture was stirred at room temperature overnight, partitioned between ethyl acetate and 1 N HCl until neutral, dried over magnesium sulfate and concentrated to provide 118 mg 5 (6-{[(allyloxy)carbonyl]amino}-1H-indole-2-carboxylic acid), as a colorless solid.

Following the procedure of Example 1 but replacing indole-2-carboxylic acid with 5 gave the title compound as a colorless solid.

EXAMPLE 9

N-[(1S,2R)-2-({[(S)-cyano(cyclopropyl)methyl]amino}carbonyl)cyclohexyl]-6-[(methylsulfonyl)amino]-1H-indole-2-carboxamide

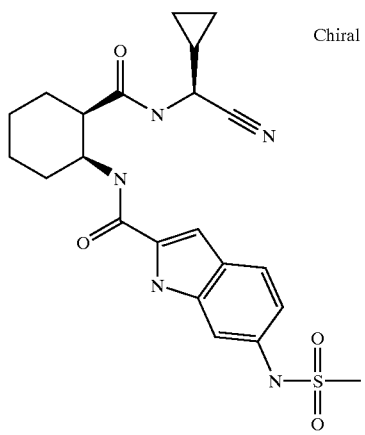

To 4.97 g (40.35 mmol) of 4-aminobenzylalcohol dissolved in 30 mL of was added 9.69 g (44.39 mmol) of di-tert-butyl dicarbonate. The mixture was stirred at at room temperature overnight, partitioned between ethyl acetate and water, dried over magnesium sulfate and concentrated to provide 8.4 g t-butyloxycarbonyl-protected 4-aminobenzyl alcohol, as a colorless solid.

To 4.79 g (21.65 mmol) of the above compound dissolved in 50 mL dichloromethane was added 9.19 g (21.65 mmol) Dess-Martin periodinane. The mixture was stirred for 2 h, partitioned between dichloromethane and water, dried over magnesium sulfate and concentrated. The product was purified using column chromatography, eluting with 25% ethyl acetate/hexane, to provide 3.0 g of 6 (tert-butyl 4-formylphenylcarbamate) as a colorless solid.

To a solution 13.45 mmol of sodium methoxide in 6 mL absolute methanol at 0° C. was added a solution of 717 mg (3.24 mmol) of 6 and 1.49 g (12.96 mmol) methylazidoacetate dissolved in 6 mL absolute methanol dropwise over 5 minutes. The mixture was stirred at 0° C. for 6 h, then partitioned between ethyl acetate and acetic acid until neutral. The organic phase was dried over magnesium sulfate, concentrated and purified by column chromatography, eluting with 25% ethyl acetate/hexane to provide 551 mg of 7 (methyl (2E)-2-azido-3-{4-[(tert-butoxycarbonyl)amino]phenyl}prop-2-enoate) as a yellow solid.

851 mg (2.67 mmol) of 7 was dissolved in 40 mL toluene. The mixture was heated to 80° C. for 2 h, cooled, and concentrated. Purification by column chromatography, eluting with 25% ethyl acetate/hexane provided 551 mg of 8 (methyl 6-[(tert-butoxycarbonyl)amino]-1H-indole-2-carboxylate) as a yellow solid.

To 551 mg 8 dissolved in 15 mL dichloromethane was added 5 mL trifluoroacetic anhydride, and the mixture stirred at room temperature for 1.5 h. P The mixture was partitioned between dichloromethane and 1 N sodium hydroxide until neutral, dried over magnesium sulfate and concentrated. Obtained 360 mg of the crude methyl 6-amino-1H-indole-2-carboxylate. To 200 mg (1.05 mmol) of crude product dissolved in 5 mL dichloromethane and 340 □L pyridine at 0° C. was added 81 □L methanesulfonyl chloride. The mixture was stirred at 0° C. for 1 h, was partitioned between dichloromethane and 1 N hydrochloric acid until neutral, was dried over magnesium sulfate and concentrated to obtain 333 mg of 9 (methyl 6-[(methylsulfonyl)amino]-1H-indole-2-carboxylate) as crude product.

To 333 mg (1.24 mmol) of 9 dissolved in 8 mL methanol was added 130 mg (3.10 mmol) lithium hydroxide dissolved in 2 mL water. The mixture was stirred at room temperature overnight, partitioned between ethyl acetate and 1 N hydrochloric acid, was dried over magnesium sulfate and concentrated to obtain 230 mg of 10 (6-[(methylsulfonyl)amino]-1H-indole-2-carboxylic acid).

Following the procedure of Example 1 but replacing indole-2-carboxylic acid with 10 gave the title compound as a colorless solid.

EXAMPLE 10

Synthesis of N-[(1S,2R)-2-({[(1S)-1-cyano-3-methylbutyl]amino}carbonyl)cyclohexyl]-1,3-benzothiazole-6-carboxamide

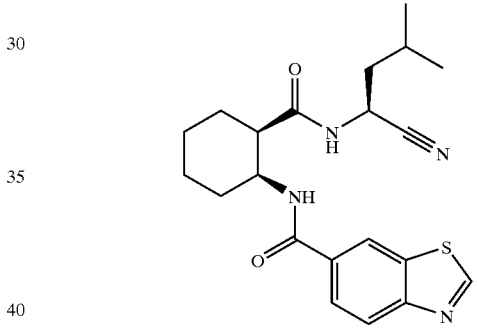

This example illustrates the synthesis of N-[(1S,2R)-2-({[(1S)-1-cyano-3-methylbutyl]amino}carbonyl)cyclohexyl]-1,3-benzothiazole-6-carboxamide starting from ethyl cis-2-amino-1-cyclohexanecarboxylate.

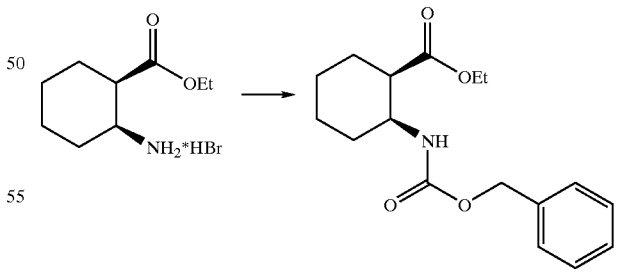

To a 0° C. solution of ethyl cis-2-amino-1-cyclohexanecarboxylate HBr salt (22.34 g, 88.6 mmol) in 250 mL of methylene chloride, was added benzylchloroformate (12.6 mL, 88.3 mmol) and 250 mL of an aqueous sodium carbonate solution. The reaction mixture was stirred for 24 h at ambient temperature. The organic layer was separated and washed with 250 mL of water, dried over sodium sulfate, filtered and concentrated to give a crude liquid. The product was purified by column chromatography (10–50:90–50 ethyl acetate/hexanes) to give 26.45 g of a clear liquid. Yield: 98%, MS: 306 (M+H⁺).

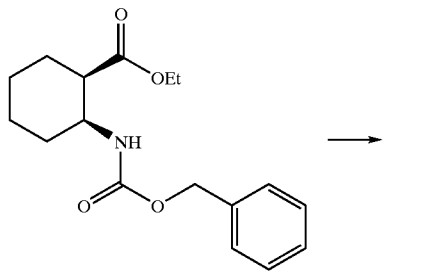

The ester (26.45 g, 86.62 mmol) was dissolved in 250 mL of tetrahydrofuran and treated with a solution of lithium hydroxide monohydrate (10.65 g, 256 mmol) in 250 mL of water and stirred at ambient temperature for 24 h. The reaction mixture was cooled to 0° C. and neutralized with 300 mL of a 1N HCl solution. Ethyl acetate (400 mL) was added and the organic layer was separated, dried over sodium sulfate, filtered and concentrated to give a crude solid. The product was purified by recrystallizing from ethyl acetate/hexanes to give 19.60 g of a white solid. Yield: 82%, MS: 278 (M+H⁺), mp=120.1–123.1° C.

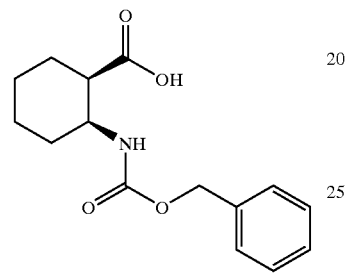

To a solution of the carboxylic acid (10.2 g, 36.9 mmol), L-Leucineamide hydrochloride (6.18 g, 40.5 mmol), EDCI hydrochloride (5.48 g, 40.6 mmol), and HOBT (5.48 g, 40.6 mmol) in 100 mL of anhydrous DMF was added N-methylmorpholine (12.0 mL, 109 mmol). The reaction mixture was stirred at ambient temperature for 24 h, then added 300 mL of water and 400 mL of ethyl acetate. The organic layer was separated and washed with two 300 mL portions of a 0.5 M HCL solution, 300 mL of water, then dried over sodium sulfate, filtered and recrystallized from ethyl acetate/hexanes to give 13.2 g of the product as a white solid. Yield: 92%, MS: 412 (M+Na⁺), mp=188.0–189.5° C.

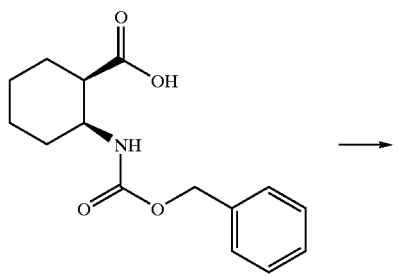

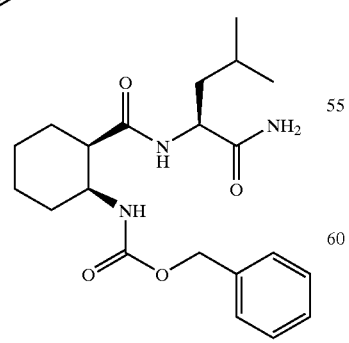

To a 0° C. solution of the amide (13.2 g, 33.9 mmol) in 150 mL of anhydrous pyridine was added trifluoroacetic anhydride (5.50 mL, 38.9 mmol) dropwise slowly over a 3 min period. The reaction mixture was stirred for 15 min and then poured into a slurry of ice and 1N HCl solution. The mixture was extracted with 500 mL of ethyl acetate, and washed with three 400 mL portions of 1N HCl, 400 mL of water, dried over sodium sulfate, filtered and concentrated to give a crude solid. Recrystallization from ethyl acetate/hexanes gave 11.3 g of the product as a white solid. Yield: 90%, MS: 394 (M+Na⁺), mp=103.6–106.5° C.

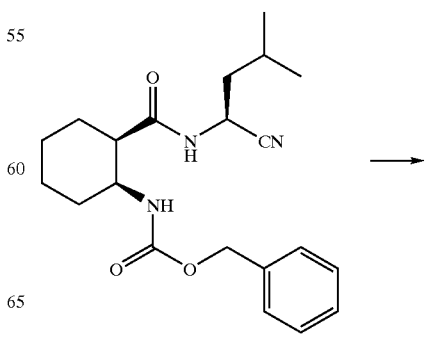

-continued

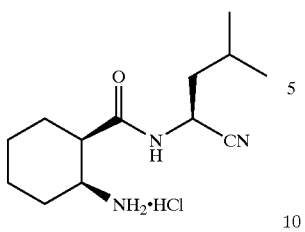

A solution of the carbamate (11.3 g, 30.4 mmol) and palladium on activated carbon (1.0 g, 10% by wt.) in 250 mL of ethyl acetate was stirred for 24 h under a hydrogen atmosphere. The reaction mixture was filtered through a pad of celite, concentrated, then treated with a 1N solution of HCl in ether (35 mL). The resulting suspension was filtered and dried to give 5.96 g of the hydrochloride salt of the product as a white hygroscopic powder. Yield: 72%, MS: 238 (M+H$^+$), mp=133.3–135.0° C.

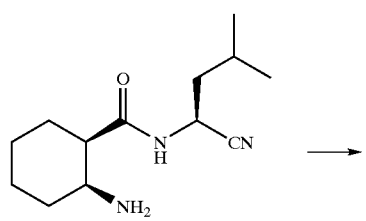

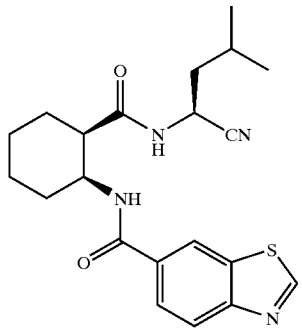

To a solution of the amine (220 mg, 0.927 mmol), 1,3-benzothiazole-6-carboxylic acid (184 mg, 1.03 mmol), EDCI hydrochloride (195 mg, 1.02 mmol), HOBT (140 mg, 1.04 mmol) in 6.0 mL of DMF was added N-methylmorpholine (0.3 mL, 2.73 mmol) and stirred at ambient temperature for 24 h. The reaction mixture was partitioned between 30 mL of water and 30 mL of ethyl acetate. The organic layer was washed with two 30 mL portions of 1N HCl solution, 30 mL of water, dried over sodium sulfate, filtered, concentrated and purified by column chromatography (methanol/methylene chloride, 3:97) to give 297 mg of the product as a white solid. Yield: 80%, MS: 399 (M+H$^+$), mp=199.6–201.2° C.

EXAMPLE 11

Synthesis of N-[(1S,2R)-2-({[(1S)-1-cyano-3-methylbutyl]amino}carbonyl)cyclohexyl]-1-(2-hydroxyethyl)-1H-indole-2-carboxamide

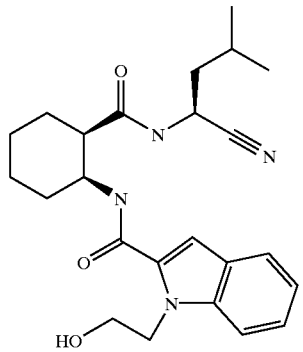

This example illustrates the synthesis of N-[(1S,2R)-2-({[(1S)-1-cyano-3-methylbutyl]amino}carbonyl)cyclohexyl]-1-(2-hydroxyethyl)-1H-indole-2-carboxamide starting from ethyl indole-2-carboxylate.

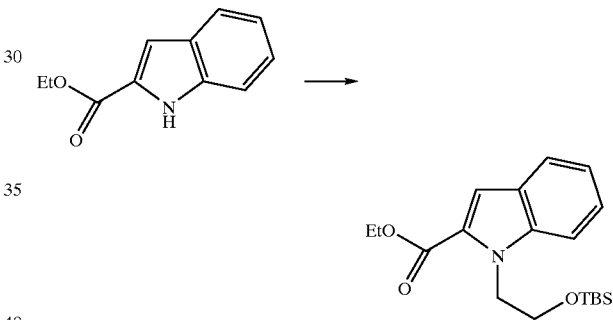

To a 0° C. solution of ethyl indole-2-carboxylate (2.82 g, 14.9 mmol) in 25 mL of anhydrous DMF, was added sodium hydride powder (0.45 g, 17.8 mmol) portionwise. The reaction mixture was stirred until gas evolution subsided (10 min), then (2-Bromoethoxy)-tert-butyldimethylsilane (3.50 mL, 16.3 mmol) was added. The reaction mixture was placed into a 30° C. oil bath for 3 h. An additional amount of (2-Bromoethoxy)-tert-butyldimethylsilane (0.50 mL, 2.33 mmol) was added and raised the oil bath temperature to 52° C. for 2 h. The cooled reaction mixture was poured into a slurry of ice water and extracted with 250 mL of ethyl acetate. The organic layer was washed with two 250 mL portions of brine, dried over sodium sulfate, filtered, concentrated, and purified by column chromatography (ethyl acetate/hexanes, 10:90) to give 3.88 g of the product as a clear liquid. Yield: 75%, MS: 348 (M+H$^+$).

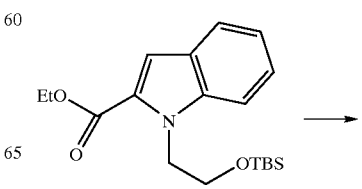

37

-continued

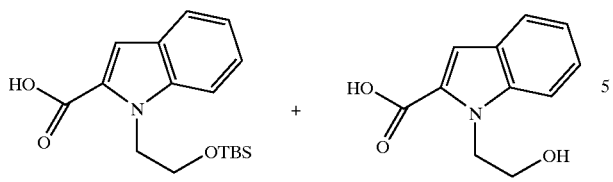

To a solution of the above ester (3.82 g, 11.0 mmol) in 40 mL of THF was treated with a solution of lithium hydroxide monohydrate (2.20 g, 52.9 mmol) in 40 mL of water and 20 mL of methanol. The reaction mixture was heated to reflux for 10 min, then cooled and stirred at ambient temperature for 2 h. The reaction mixture was poured onto a slurry of ice and a 1N HCl solution, and extracted with 50 mL of ethyl acetate. The organic layer was washed with 100 mL of water, dried over sodium sulfate, filtered and concentrated to give 2.50 g of a white solid as a 1:1 mixture of two carboxylic acid products (as determined by $^1$H NMR spectroscopy). The mixture was used in the next coupling without further purification.

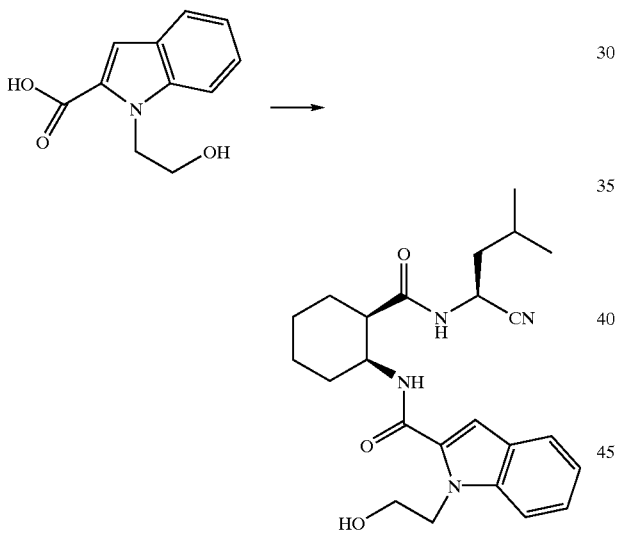

The above carboxylic acid (0.67 g, 1.63 mmol, as a 1:1 mixture of alcohol/silylether, see previous scheme), amine (0.45 g, 1.90 mmol), EDCI hydrochloride (0.42 g, 2.20 mmol), HOBT (0.28 g, 2.07 mmol), and N-methylmorpholine (0.50 mL, 4.55 mmol) in 18 mL of anhydrous DMF, were stirred at ambient temperature for 24 h. The reaction mixture was partitioned between 50 mL of water and 50 mL of ethyl acetate. The organic layer was washed with two 50 mL portions of 1N HCl solution, 50 mL of water, then dried over sodium sulfate, filtered, concentrated and purified by column chromatography (40:60 ethyl acetate/hexanes) to give 184 mg of the product as a white foam solid. Yield: 27%, MS: 425.2 (M+H$^+$), mp=59.0–63.5° C.

38

EXAMPLE 12

N-[(1S,2R)-2-({[(1S)-1-cyano-3-methylbutyl]amino}carbonyl)cyclohexyl]-1-methyl-6-(2-pyridin-2-ylethoxy)-1H-indole-2-carboxamide, Compound 4-3

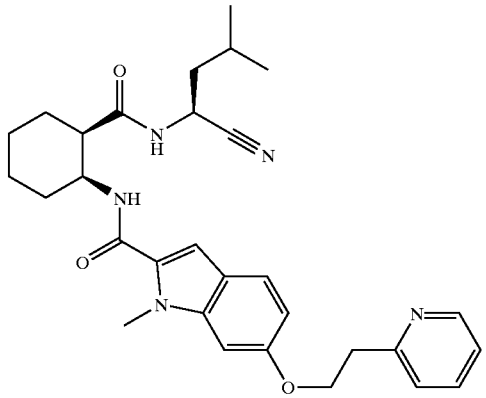

This compound was prepared by a modification of method B-2. An intermediate in Method B-2, N-[(1S,2R)-2-({[(1S)-1-carboxamide-3-methylbutyl]amino}carbonyl)cyclohexyl]-6-hydroxy-1-methyl-1H-indole-2-carboxamide, was subjected to a Mitsonobu coupling.

Mitsunobu Coupling

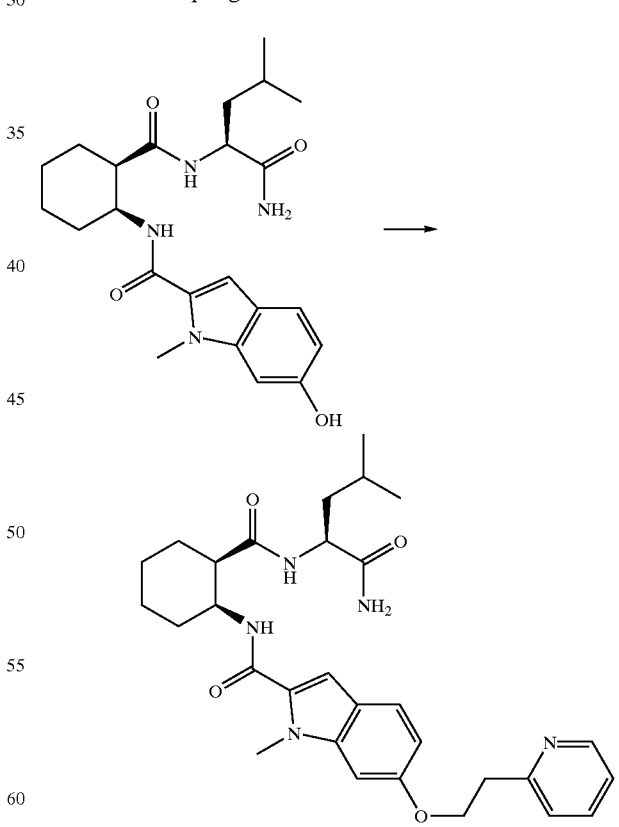

To a flask under nitrogen was added 0.10 gm (0.23 mm) N-[(1S,2R)-2-({[(1S)-1-carboxamide-3-methylbutyl]amino}carbonyl)cyclohexyl]-6-hydroxy-1-methyl-1H-indole-2-carboxamide, 0.122 gm (0.47 mm) triphenylphosphine and 0.057 gm (0.47 mm) 2-pyridin-2-ylethanol along with 3 ml Dimethylfornamide. The flask was cooled in an ice-salt bath. 0.074 ml (0.47 mm) Diethyl azodicarboxylate was added in four portions once every twenty minutes. An additional 0.122 gm Triphenylphosphine, 0.057 gm 2-pyridin-2-ylethanol and 0.074 ml Diethyl azodicarboxylate was added in the same fashion. After stirring overnight at room temperature an additional 0.122 gm triphenylphosphine and 0.074 ml diethylazodicarboxlyate were added at room temperature. The reaction mixture was concentrated under vacuum to remove solvent and 25 ml ethyl acetate was added. This was extracted three times with 25 ml of 0.1M hydrochloric acid, the organic layer discarded and the extracts were treated with aqueous sodium carbonate to a pH of 8 and extracted three times with 25 ml ethyl acetate. The extracts were dried over magnesium sulfate, solvent was removed under vacuum and the residue purified on a silica gel preparative TLC plate eluting with 5% methanol 95% dichloromethane to give N-[(1S,2R)-2-({[(1S)-1-carboxamide-3-methylbutyl]amino}carbonyl)cyclohexyl]-1-methyl-6-(2-pyridin-2-ylethoxy)-1H-indole-2-carboxamide.

This product, N-[(1S,2R)-2-({[(1S)-1-carboxamide-3-methylbutyl]amino}carbonyl)cyclohexyl]-1-methyl-6-(2-pyridin-2-ylethoxy)-1H-indole-2-carboxamide is converted by the final step of Method B-2 into the desired N-[(1S,2R)-2-({[(1S)-1-cyano-3-methylbutyl]amino}carbonyl)cyclohexyl]-1-methyl-6-(2-pyridin-2-ylethoxy)-1H-indole-2-carboxamide

EXAMPLE 13

Synthesis of Intermediates

6-Hydroxy-1-methyl-1H-indole-2-carboxylic acid

This carboxylic acid was used to prepare compounds 2-4, 2-6, 2-14, 2-18, 2-19, 4-2, 4-3 and 4-4.

Step 1. N-Methylation

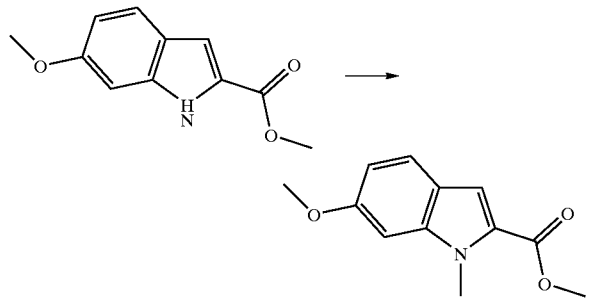

To a flask under nitrogen was added 3.0 grams (60%, 75.2 mM) sodium hydride. The solid was rinsed twice with hexane and 30 ml DMF was added. A solution of 14.03 g (68.4 mM) 6-Methoxy-1H-indole-2-carboxylic acid methyl e ster in 15 ml DMF was added in portions. After the gas evolution had stopped the mixture was chilled in an ice bath and 14.07 g (99.13 mM)g iodomethane mixed with 5 ml DMF was added. The mixture was allowed to warm to room temperature and stir overnight. The reaction was quenched with water and a small amount of aqueous HCl. The DMF was removed under vacuum and the residue partitioned between water and ethyl acetate. The ethyl acetate layer was dried over magnesium sulfate, stripped and the solid purified by column chromatography on silica gel. (gradient of 10 to 30% Ethyl acetate/hexane) to give 6-Methoxy-1-methyl-1H-indole-2-carboxylic acid methyl ester, 13.47 g, (M/S 220.2, M+H) as a white solid. This compound was hydrolysed to the carboxylic acid and used to prepare compounds 1-24, 1-33, 1-34, and 2-15.

Step 2. Cleavage of 6-Methoxy Group and methyl ester.

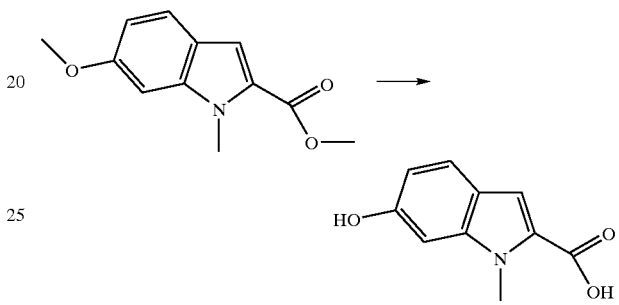

To a flask under nitrogen was added 576 mg (2.63 mM) of 6-Methoxy-1-methyl-1H-indole-2-carboxylic acid methyl ester and 30 ml dichloromethane. The mixture was cooled to −60° C. in dry ice acetone bath and 16 ml 1M boron tribromide in dichloromethane (16 mM) was added. After stirring 45 minutes at −60° C. the mixture was allowed to warm to room temperature and stirred for 5 hours. The mixture was poured into 200 ml saturated sodium bicarbonate solution and stirred for 30 minutes. Hydrochloric acid was added till acidic, ethyl acetate was added and the mixture filtered through a celite plug to remove insoluble solids. The ethyl acetate layer was separated and the aqueous was extracted two more time with ethyl acetate. The combined ethyl acetate layers were dried over magnesium sulfate, filtered and stripped to give 6-Hydroxy-1-methyl-1H-indole-2-carboxylic acid (M/S, ES-, 190.2 M-H)

6-Hydroxy-1H-indole-2-carboxylic acid

6-Methoxy-1H-indole-2-carboxylic acid methyl ester when subjected to Step 2 gave 6-hydroxy-1H-indole-2-carboxylic acid which was used in the preparation of compounds 2-5, 2-13, 2-17, and 2-19.

Compound Tables

Several compounds of general formula (I) have been prepared by the methods described in the preceding Examples. The following Tables shows their structures, analytical data and the method used for the preparation.

COMPOUND TABLE 1

| Cpd # | Structure | Compound Name | Method | Educt 1 | Educt 2 | MW | MS |
|---|---|---|---|---|---|---|---|
| 1-1 | 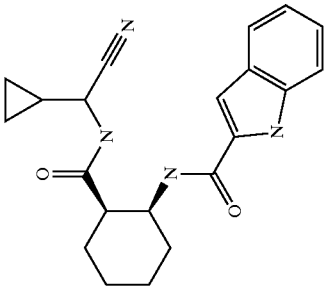 Chiral | N-[(1S,2R)-2-({[cyano(cyclopropyl)methyl]amino}carbonyl)cyclohexyl]-1H-indole-2-carboxamide | A | (1R,2S)-2-[(1H-indol-2-yl)carbonyl]amino]cyclohexanecarboxilic acid | R,S-amino(cyclopropyl)acetonitrile | 364.44 | 364 |
| 1-2 | 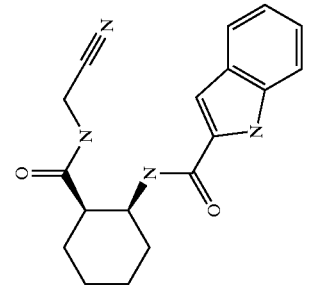 | N-((1S,2R)-2-{[(cyanomethyl)amino]carbonyl}cyclohexyl)-1H-indole-2-carboxamide | A | (1R,2S)-2-[(1H-indol-2-yl)carbonyl]amino]cyclohexanecarboxilic acid | Amino-acetonitrile | 324.38 | 324 |
| 1-3 | 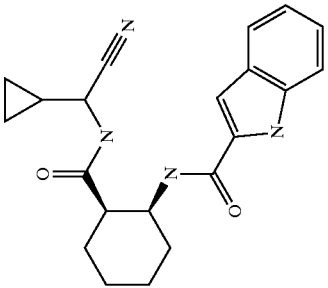 | N-[(1S,2R)-2-({[cyano(cyclopropyl)methyl]amino}carbonyl)cyclohexyl]-1H-indole-2-carboxamide | A | (1R,2S)-2-[(1H-indol-2-yl)carbonyl]amino]cyclohexanecarboxilic acid | 364.45 | 364 | |

COMPOUND TABLE 1-continued

| Cpd # | Structure | Compound Name | Method | Educt 1 | Educt 2 | MW | MS |
|---|---|---|---|---|---|---|---|
| 1-4 | 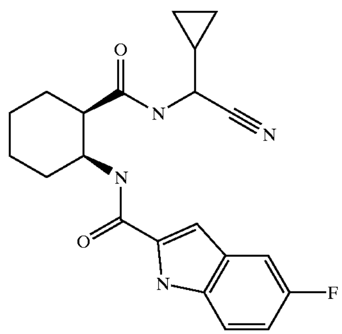 | N-[(1S,2R)-2-({[cyano(cyclopropyl)methyl]amino}carbonyl)cyclohexyl]-5-fluoro-1H-indole-2-carboxamide | A | (1R,2S)-2-[(5-fluoro-1H-indol-2-ylcabonyl)amino]cyclohexanecarboxilic acid | R,S-amino(cyclopropyl)acetonitrile | 382.44 | 382 |
| 1-5 | 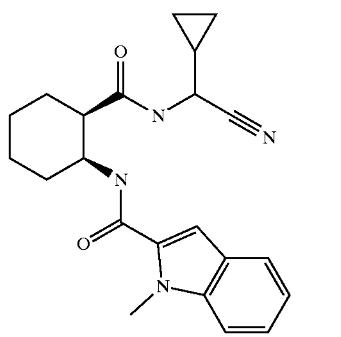 | N-[(1S,2R)-2-({[cyano(cyclopropyl)methyl]amino}carbonyl)cyclohexyl]-1-methyl-1H-indole-2-carboxamide | A | (1R,2S)-2-[(1-methyl-1H-indol-2-ylcabonyl)amino]cyclohexanecarboxilic acid | R,S-amino(cyclopropyl)acetonitrile | 378.48 | 378 |
| 1-6 | 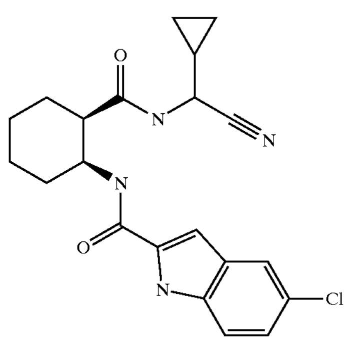 | 5-chloro-N-[(1S,2R)-2-({[cyano(cyclopropyl)methyl]amino}carbonyl)cyclohexyl]-1H-indole-2-carboxamide | A | (1R,2S)-2-[(5-chloro-1H-indol-2-ylcabonyl)amino]cyclohexanecarboxilic acid | R,S-amino(cyclopropyl)acetonitrile | 398.9 | 398 |

COMPOUND TABLE 1-continued

| Cpd # | Structure | Compound Name | Method | Educt 1 | Educt 2 | MW | MS |
|---|---|---|---|---|---|---|---|
| 1-7 | 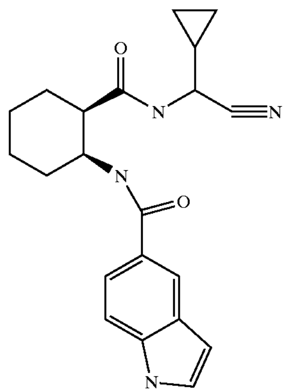 | N-[(1S,2R)-2-({[cyano cyclopropyl)methyl]amino} carbonyl)cyclohexyl]-1H-indole-5-carboxamide | A | (1R,2S)-2-[(1H-indol-5-yl)carbonyl]amino] cyclohexanecarboxilic acid | R,S-amino (cyclopropyl) acetonitrile | 364.45 | 364 |
| 1-8 | 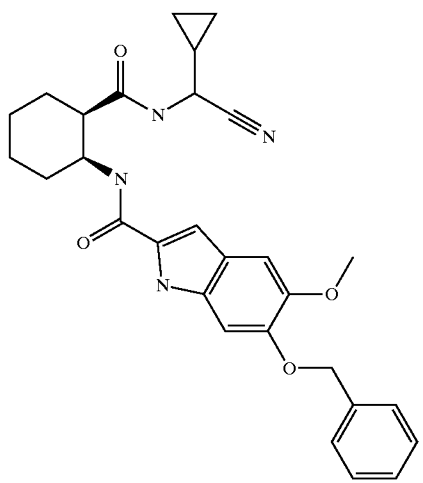 | 6-(benzyloxy)-N-[(1S,2R)-2-({[cyano(cyclopropyl)methyl] amino}carbonyl)cyclohexyl]-5-methoxy-1H-indole-2-carboxamide | A | (1R,2S)-2-[(6-Benzyloxy-5-methoxy-1H-indole-2-carbonyl)-amino]-cyclohexane-carboxylic acid | R,S-amino (cyclopropyl) acetonitrile | 500.59 | 500 |

COMPOUND TABLE 1-continued

| Cpd # | Structure | Compound Name | Method | Educt 1 | Educt 2 | MW | MS |
|---|---|---|---|---|---|---|---|
| 1-9 | 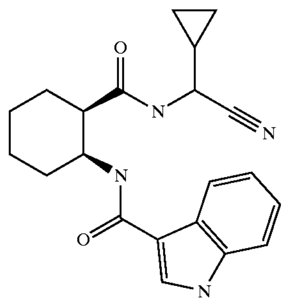 | N-[(1S,2R)-2-([[cyano(cyclopropyl)methyl]amino]carbonyl)cyclohexyl]-1H-indole-3-carboxamide | A | (1R,2S)-2-[(1H-Indole-3-carbonyl)-amino]-cyclohexane-carboxylic acid | R,S-amino(cyclopropyl)acetonitrile | 364.44 | 364 |
| 1-10 | 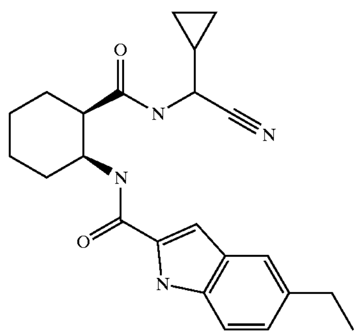 | N-[(1S,2R)-2-([[cyano(cyclopropyl)methyl]amino]carbonyl)cyclohexyl]-5-ethyl-1H-indole-2-carboxamide | A | (1R,2S)-2-[(5-Ethyl-1H-indole-2-carbonyl)-amino]-cyclohexane-carboxylic acid | R,S-amino(cyclopropyl)acetonitrile | 392.5 | 392 |
| 1-11 | 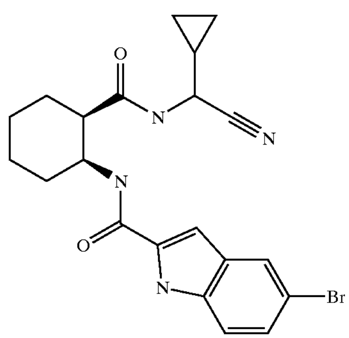 | 5-bromo-N-[(1S,2R)-2-([[cyano(cyclopropyl)methyl]amino]carbonyl)cyclohexyl]-1H-indole-2-carboxamide | A | (1R,2S) 2-[(5-Bromo-1H-indole-2-carbonyl)-amino]-cyclohexane-carboxylic acid | R,S-amino(cyclopropyl)acetonitrile | 443.34 | 443 |

COMPOUND TABLE 1-continued

| Cpd # | Structure | Compound Name | Method | Educt 1 | Educt 2 | MW | MS |
|---|---|---|---|---|---|---|---|
| 1-12 | 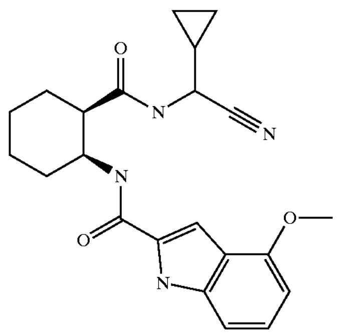 | N-[(1S,2R)-2-([[cyano(cyclopropyl)methyl]amino]carbonyl)cyclohexyl]-4-methoxy-1H-indole-2-carboxamide | A | (1R,2S)-2-[(4-Methoxy-1H-indole-2-carbonyl)-amino]-cyclohexane-carboxylic acid | R,S-amino(cyclopropyl)acetonitrile | 394.47 | 394 |
| 1-13 | 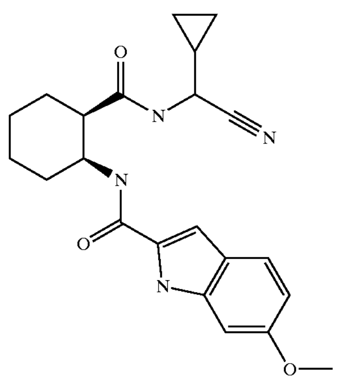 | N-[(1S,2R)-2-([[cyano(cyclopropyl)methyl]amino]carbonyl)cyclohexyl]-6-methoxy-1H-indole-2-carboxamide | A | (1R,2S)-2-[(6-Methoxy-1H-indole-2-carbonyl)-amino]-cyclohexane-carboxylic acid | R,S-amino(cyclopropyl)acetonitrile | 394.47 | 394 |
| 1-14 | 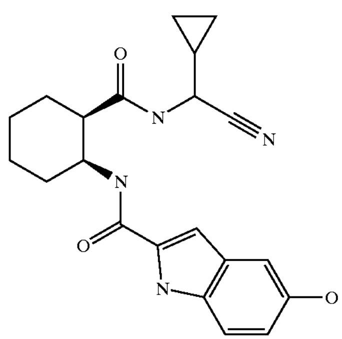 | N-[(1S,2R)-2-([[cyano(cyclopropyl)methyl]amino]carbonyl)cyclohexyl]-5-hydroxy-1H-indole-2-carboxamide | A | (1R,2S)-2-[(5-Hydroxy-1H-indole-2-carbonyl)-amino]-cyclohexane-carboxylic acid | R,S-amino(cyclopropyl)acetonitrile | 380.44 | 380 |

COMPOUND TABLE 1-continued

| Cpd # | Structure | Compound Name | Method | Educt 1 | Educt 2 | MW | MS |
|---|---|---|---|---|---|---|---|
| 1-15 | 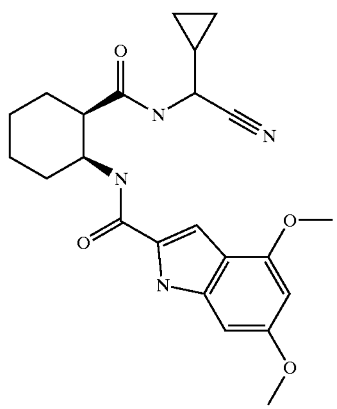 | N-[(1S,2R)-2-({[cyano(cyclopropyl)methyl]amino}carbonyl)cyclohexyl]-4,6-dimethoxy-1H-indole-2-carboxamide | A | (1R,2S)-2-[(4,6-Dimethoxy-1H-indole-2-carbonyl)amino]-cyclohexane-carboxylic acid | R,S-amino(cyclopropyl)acetonitrile | 424.49 | 424 |
| 1-16 | 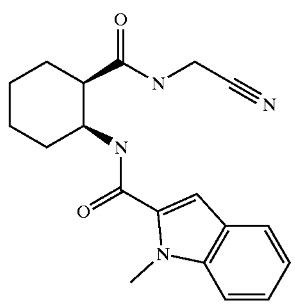 | N-((1S,2R)-2-{[(cyanomethyl)amino]carbonyl}cyclohexyl)-1-methyl-1H-indole-2-carboxamide | A | (1R,2S)-2-[(1-Methyl-1H-indole-2-carbonyl)amino]-cyclohexane-carboxylic acid | Amino-acetonitrile | 338.40 | 338 |

COMPOUND TABLE 1-continued

| Cpd # | Structure | Compound Name | Method | Educt 1 | Educt 2 | MW | MS |
|---|---|---|---|---|---|---|---|
| 1-17 | Chiral | N-[(1S,2R)-2-{[(cyanomethyl)amino]carbonyl}cyclohexyl]-6-(methylthio)-1H-indole-2-carboxamide | A | (1R,2S)-2-[(6-Methylsulfanyl-1H-indole-2-carbonyl)-amino]-cyclohexane-carboxylic acid | Amino-acetonitrile | 370.47 | 370 |
| 1-18 | 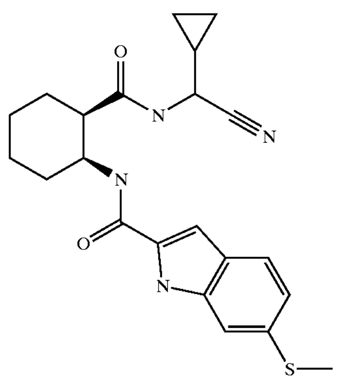 | N-[(1S,2R)-2-({[cyano(cyclopropyl)methyl]amino}carbonyl)cyclohexyl]-6-(methylthio)-1H-indole-2-carboxamide | A | (1R,2S)-2-[(6-Methylsulfanyl-1H-indole-2-carbonyl)-amino]-cyclohexane-carboxylic acid | R,S-amino(cyclopropyl)acetonitrile | 410.53 | 410 |

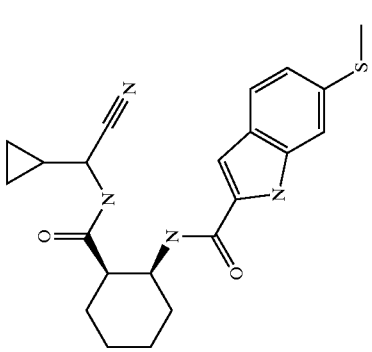

COMPOUND TABLE 1-continued

| Cpd # | Structure | Compound Name | Method | Educt 1 | Educt 2 | MW | MS |
|---|---|---|---|---|---|---|---|
| 1-19 | 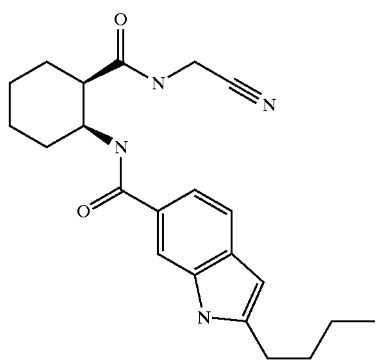 | 2-butyl-N-((1S,2R)-2-{[(cyanomethyl)amino]carbonyl}cyclohexyl)-1H-indole-6-carboxamide | A | (1R,2S)-2-[(2-Butyl-1H-indole-6-carbonyl)-amino]-cyclohexane-carboxylic acid | Amino-acetonitrile | 380.48 | 380 |
| 1-20 | 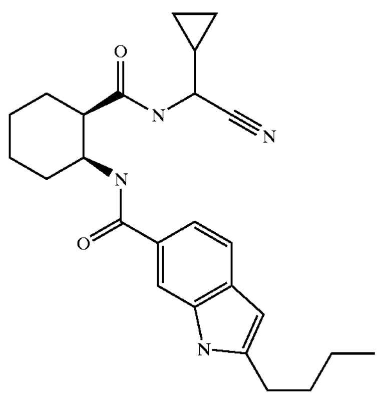 | 2-butyl-N-[(1S,2R)-2-({[cyano(cyclopropyl)methyl]amino}carbonyl)cyclohexyl]-1H-indole-6-carboxamide | A | (1R,2S)-2-[(2-Butyl-1H-indole-6-carbonyl)-amino]-cyclohexane-carboxylic acid | R,S-amino(cyclopropyl)acetonitrile | 420.55 | 420 |

COMPOUND TABLE 1-continued

| Cpd # | Structure | Compound Name | Method | Educt 1 | Educt 2 | MW | MS |
|---|---|---|---|---|---|---|---|
| 1-21 | 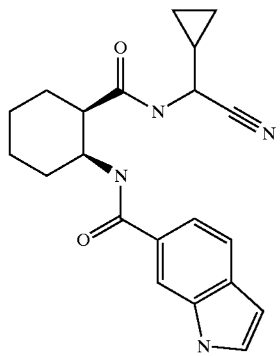 | N-[(1S,R)-2-({[cyano(cyclopropyl)methyl]amino}carbonyl)cyclohexyl]-1H-indole-6-carboxamide | A | (1R,2R)-2-[(1H-Indole-6-carbonyl)-amino]-cyclohexane-carboxylic acid | R,S-amino(cyclopropyl)acetonitrile | 364.44 | 364 |
| 1-22 | 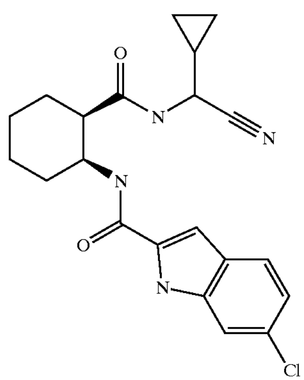 | 6-chloro-N-[(1S,2R)-2-({[cyano(cyclopropyl)methyl]amino}carbonyl)cyclohexyl]-1H-indole-2-carboxamide | A | (1R,2S)-2-[(6-Chloro-1H-indole-2-carbonyl)-amino]-cyclohexane-carboxylic acid | R,S-amino(cyclopropyl)acetonitrile | 398.89 | 398 |

COMPOUND TABLE 1-continued

| Cpd # | Structure | Compound Name | Method | Educt 1 | Educt 2 | MW | MS |
|---|---|---|---|---|---|---|---|
| 1-23 | 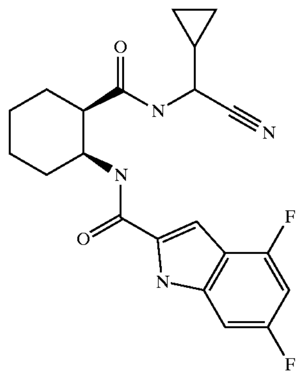 | N-[(1S,2R)-2-({[cyano(cyclopropyl)methyl]amino}carbonyl)cyclohexyl]-4,6-difluoro-1H-indole-2-carboxamide | A | (1R,2S)-2-[(4,6-Difluoro-1H-indole-2-carbonyl)-amino]-cyclohexane-carboxylic acid | R,S-amino(cyclopropyl)acetonitrile | 400.42 | 400 |
| 1-24 | 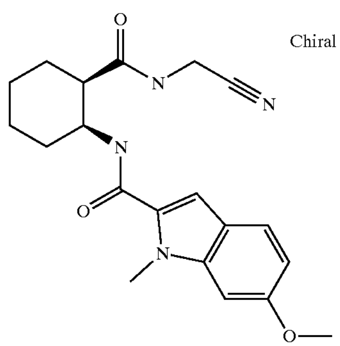 | N-((1S,2R)-2-{[(cyanomethyl)amino]carbonyl}cyclohexy)-6-methoxy-1-methyl-1H-indole-2-carboxamide | A | (1R,2S)-2-[(6-Methoxy-1-methyl-1H-indole-2-carbonyl)-amino]-cyclohexane-carboxylic acid | Amino-acetonitrile | 368.43 | 368 |
| 1-25 | 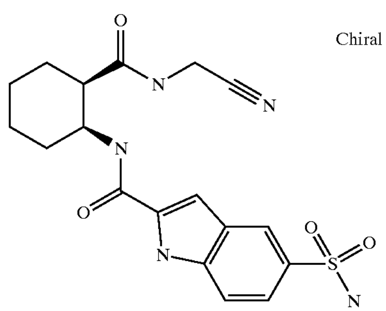 | 5-(aminosulfonyl)-N-((1S,2R)-2-{[(cyanomethyl)amino]carbonyl}cyclohexyl)-1H-indole-2-carboxamide | A | (1R,2S)-2-[(5-Sulfamoyl-1H-indole-2-carbonyl)-amino]-cyclohexane-carboxylic acid | Amino-acetonitrile | 403.46 | 403 |

COMPOUND TABLE 1-continued

| Cpd # | Structure | Compound Name | Method | Educt 1 | Educt 2 | MW | MS |
|---|---|---|---|---|---|---|---|
| 1-26 | 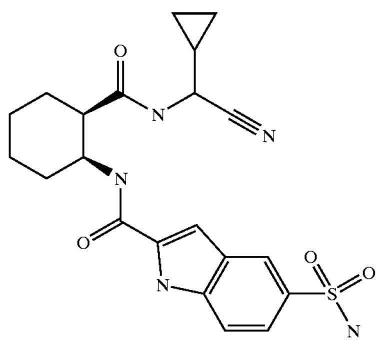 | 5-(aminosulfonyl)-N-[(1S,2R)-2-({[cyano(cyclopropyl)methyl]amino}carbonyl)cyclohexyl]-1H-indole-2-carboxamide | A | (1R,2S)-2-[(5-Sulfamoyl-1H-indole-2-carbonyl)-amino]-cyclohexane-carboxylic acid | R,S-amino(cyclopropyl)acetonitrile | 443.5 | 443 |
| 1-27 | 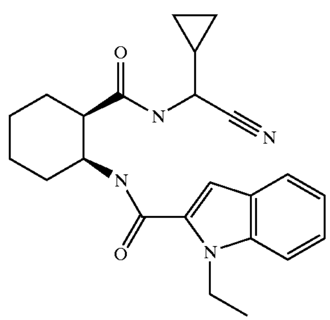 | N-[(1S,2R)-2-({[cyano(cyclopropyl)methyl]amino}carbonyl)cyclohexyl]-1-ethyl-1H-indole-2-carboxamide | A | (1R,2S)-2-[(1-Ethyl-1H-indole-2-carbonyl)-amino]-cyclohexane-carboxylic acid | R,S-amino(cyclopropyl)acetonitrile | 392.5 | 392 |
| 1-28 | 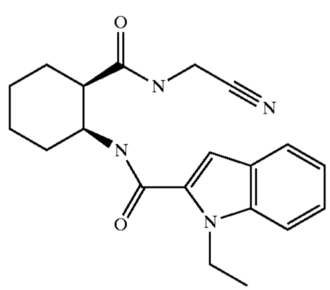 | N-((1S,2R)-2-{[(cyanomethyl)amino]carbonyl}cyclohexyl)-1-ethyl-1H-indole-2-carboxamide | A | (1R,2S)-2-[(1-Ethyl-1H-indole-2-carbonyl)-amino]-cyclohexane-carboxylic acid | Amino-acetonitrile | 352.4 | 352 |

COMPOUND TABLE 1-continued

| Cpd # | Structure | Compound Name | Method | Educt 1 | Educt 2 | MW | MS |
|---|---|---|---|---|---|---|---|
| 1-29 | Chiral | N-[(1S,2R)-2-({[(S)-cyano(cyclopropyl)methyl]amino}carbonyl)cyclohexyl]-1-methyl-1H-indole-2-carboxamide | B-2 | (1R,2S)-2-[(1-Methyl-1H-indole-2-carbonyl)amino]-cyclohexane-carboxylic acid | (S)-cyclopropyl-glycinamide | 378.4 | 378 |
| 1-30 | Chiral | N-[(1S,2R)-2-({[(R)-cyano(cyclopropyl)methyl]amino}carbonyl)cyclohexyl]-1-methyl-1H-indole-2-carboxamide | B-2 | (1R,2S)-2-[(1-Methyl-1H-indole-2-carbonyl)amino]-cyclohexane-carboxylic acid | (R)-cyclopropyl-glycinamide | 378.4 | 378 |
| 1-31 | Chiral | N-[(1S,2R)-2-({[(1S)-1-cyano-2-thien-3-ylethyl]amino}carbonyl)cyclohexyl]-1H-indole-2-carboxamide | B-1 | (1R,2S)-2-[(1H-Indole-2-carbonyl)amino]-cyclohexane-carboxylic acid | (2S)-2-Amino-3-thiophen-3-yl-propionamide | 420.5 | 420 |

COMPOUND TABLE 1-continued

| Cpd # | Structure | Compound Name | Method | Educt 1 | Educt 2 | MW | MS |
|---|---|---|---|---|---|---|---|
| 1-32 | Chiral | N-[(1S,2R)-2-({[(1S)-1-cyano-2-thien-3-ylethyl]amino}carbonyl)cyclohexyl]-1H-indole-5-carboxamide | B-1 | (1R,2S)-2-[(1H-Indole-5-carbonyl)-amino]-cyclohexane-carboxylic acid | (2S)-2-Amino-3-thiophen-3-yl-propionamide | 420.5 | 420 |
| 1-33 | Chiral | N-[(1S,2R)-2-({[(S)-cyano(cyclopropyl)methyl]amino}carbonyl)cyclohexyl]-6-methoxy-1-methyl-1H-indole-2-carboxamide | B-2 | (1R,2S)-2-[(6-Methoxy-1-methyl-1H-indole-2-carbonyl)-amino]-cyclohexane-carboxylic acid | (S)-cyclopropyl-glycineamide | 408.4 | 408 |

COMPOUND TABLE 1-continued

| Cpd # | Structure | Compound Name | Method | Educt 1 | Educt 2 | MW | MS |
|---|---|---|---|---|---|---|---|
| 1-34 | Chiral | N-[(1S,2R)-2-({[(1S)-1-cyano-2-phenylethyl]amino}carbonyl)cyclohexyl]-6-methoxy-1-methyl-1H-indole-2-carboxamide | B-2 | (1R,2S)-6-Methoxy-1-methyl-1H-indole-2-carboxylic acid (2-carbamoyl-cyclohexyl)-amide | L-phenylalanin-amide | 458.5 | 458 |
| 1-35 | 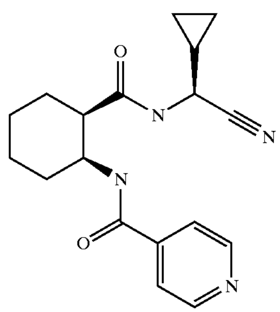 | N-[(1S,2R)-2-({[cyano(cyclopropyl)methyl]amino}carbonyl)cyclohexyl]isonicotinamide | A | (1S,2R)-2-[(Pyridine-4-carbonyl)-amino]-cyclohexane-carboxylic acid | R,S-amino(cyclopropyl)acetonitrile | 326.3 | 326 |

COMPOUND TABLE 1-continued

| Cpd # | Structure | Compound Name | Method | Educt 1 | Educt 2 | MW | MS |
|---|---|---|---|---|---|---|---|
| 1-36 | 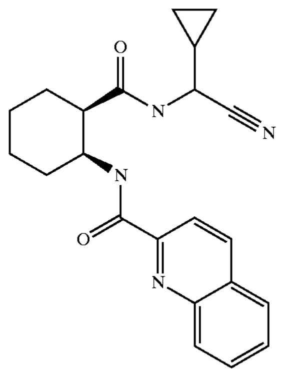 | N-[(1S,2R)-2-({[cyano(cyclopropyl)methyl]amino}carbonyl)cyclohexyl]quinoline-2-carboxamide | A | (1R,2S)-2-[(Quinoline-2-carbonyl)-amino]-cyclohexane-carboxylic acid | R,S-amino(cyclopropyl)acetonitrile | 376.4 | 376 |
| 1-37 | 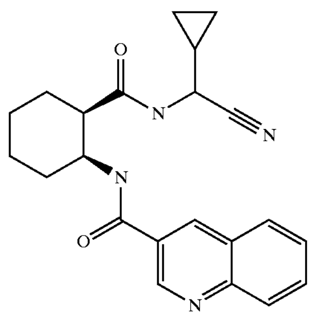 | N-[(1S,2R)-2-({[cyano(cyclopropyl)methyl]amino}carbonyl)cyclohexyl]quinoline-3-carboxamide | A | (1R,2S)-2-[(Quinoline-3-carbonyl)-amino]-cyclohexane-carboxylic acid | R,S-amino(cyclopropyl)acetonitrile | 376.4 | 376 |

COMPOUND TABLE 1-continued

| Cpd # | Structure | Compound Name | Method | Educt 1 | Educt 2 | MW | MS |
|---|---|---|---|---|---|---|---|
| 1-38 | 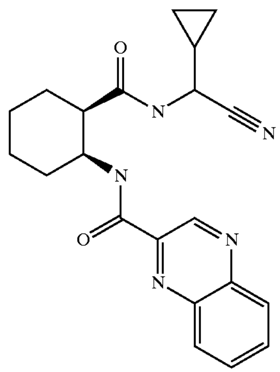 | N-[(1S,2R)-2-({[cyano(cyclopropyl)methyl]amino}carbonyl)cyclohexyl]quinoxaline-2-carboxamide | A | (1R,2S)-2-[(Quinoxaline-2-carbonyl)-amino]-cyclohexane-carboxylic acid | R,S-amino(cyclopropyl)acetonitrile | 377.4 | 377 |
| 1-39 | 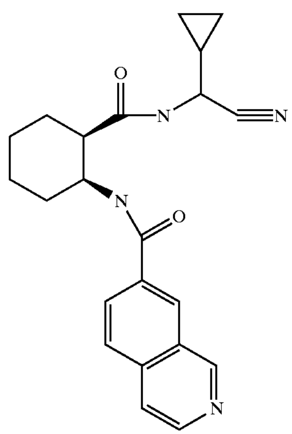 | N-[(1S,2R)-2-({[cyano(cyclopropyl)methyl]amino}carbonyl)cyclohexyl]isoquinoline-7-carboxamide | A | (1R,2S)-2-[(Isoquinoline-7-carbonyl)-amino]-cyclohexane-carboxylic acid | R,S-amino(cyclopropyl)acetonitrile | 376.4 | 376 |

COMPOUND TABLE 1-continued

| Cpd # | Structure | Compound Name | Method | Educt 1 | Educt 2 | MW | MS |
|---|---|---|---|---|---|---|---|
| 1-40 | 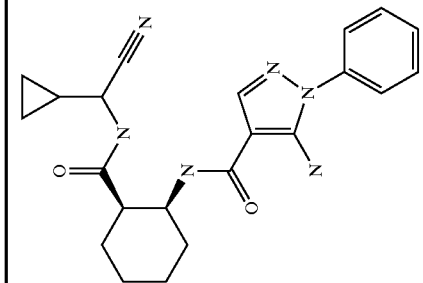 | 5-amino-N-[(1S,2R)-2-({[cyano(cyclopropyl)methyl]amino}carbonyl)cyclohexyl]-1-phenyl-1H-pyrazole-4-carboxamide | A | (1R,2S)-2-[(5-Amino-1-phenyl-1H-pyrazole-4-carbonyl)-amino]-cyclohexane-carboyxlic acid | R,S-amino(cyclopropyl)acetonitrile | 406.4 | 406 |
| 1-41 | 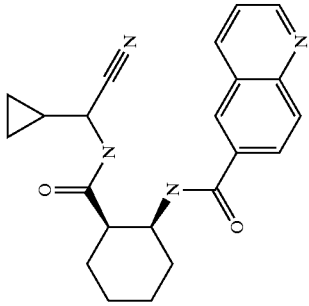 | N-[(1S,2R)-2-({[cyano(cyclopropyl)methyl]amino}carbonyl)cyclohexyl]quinoline-6-carboxamide | A | (1R,2S)-2-[(Quinoline-6-carbonyl)-amino]-cyclohexane-carboxylic acid | R,S-amino(cyclopropyl)acetonitrile | 376.4 | 376 |

COMPOUND TABLE 1-continued

| Cpd # | Structure | Compound Name | Method | Educt 1 | Educt 2 | MW | MS |
|---|---|---|---|---|---|---|---|
| 1-42 | Chiral 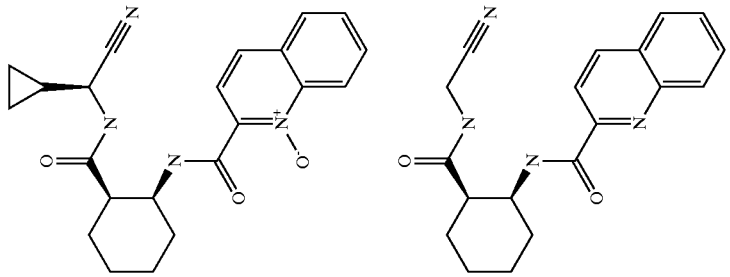 | N-[(1S,2R)-2-([(S)-cyano(cyclopropyl)methyl]amino}carbonyl)cyclohexyl]quinoline-2-carboxamide 1-oxide | A | (1R,2S)-2-[(1-Oxy-quinoline-2-carbonyl)-amino]-cyclohexane-carboxylic acid | (R)-amino(cyclopropyl)acetonitrile | 392.4 | 392 |
| 1-43 | 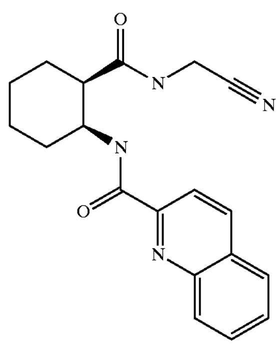 | N-((1S,2R)-2-{[(cyanomethyl)amino]carbonyl}cyclohexyl)quinoline-2-carboxamide | A | (1R,2S)-2-[(Quinoline-2-carbonyl)-amino]-cyclohexane-carboxylic acid | Amino-acetonitrile | 336.3 | 336 |

COMPOUND TABLE 1-continued

| Cpd # | Structure | Compound Name | Method | Educt 1 | Educt 2 | MW | MS |
|---|---|---|---|---|---|---|---|
| 1-44 | Chiral | N-[(1S,2R)-2-({[(1S)-1-cyano-2-phenylethyl]amino}carbonyl)cyclohexyl]quinoline-2-carboxamide | B-1 | (1R,2S)-2-[(Quinoline-2-carbonyl)-amino]-cyclohexane-carboxylic acid | (2S)-2-Amino-3-phenyl-propionamide | 426.5 | 426 |
| 1-45 | Chiral | N-[(1S,2R)-2-({[(1S)-1-cyano-2-phenylethyl]amino}carbonyl)cyclohexyl]quinoxaline-2-carboxamide | B-1 | (1R,2S)-2-[(Quinoxaline-2-carbonyl)-amino]-cyclohexane-carboxylic acid | (2S)-2-Amino-3-phenyl-propionamide | 427.5 | 427 |

COMPOUND TABLE 2

| Cpd # | Structure | Compound Name | Method | MW | M/S |
|---|---|---|---|---|---|
| 2-1 | 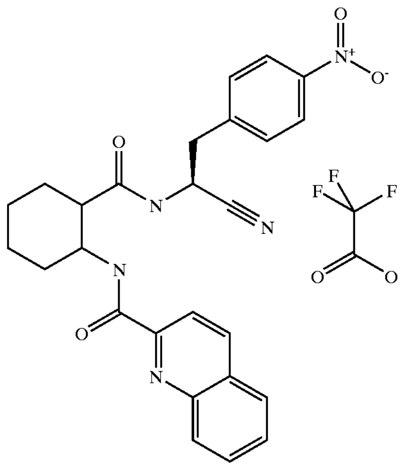 | N-[2-({[(1S)-1-cyano-2-(4-nitrophenyl)ethyl]amino}carbonyl)cyclohexyl]quinoline-2-carboxamide trifluoroacetate | C | 471.5 | 471 |
| 2-2 | Chiral | N-[(1S,2R)-2-({[(1S)-1-cyano-2-methylpropyl]amino}carbonyl)cyclohexyl]-1-methyl-1H-indole-2-carboxamide | B-2 | 380.489 | 380 |
| 2-3 | Chiral | tert-butyl-2-({[(1S,2R)-2-({[(S)-cyano(cyclopropyl)methyl]amino}carbonyl)cyclohexyl]amino}carbonyl)-1H-indol-5-ylcarbamate | A | 479.578 | 479 |
| 2-4 | Chiral | N-((1S,2R)-2-{[(cyanomethyl)amino]carbonyl}cyclohexyl)-6-hydroxy-1-methyl-1H-indole-2-carboxamide | A | 354.408 | 354 |

COMPOUND TABLE 2-continued

| Cpd # | Structure | | Compound Name | Method | MW | M/S |
|---|---|---|---|---|---|---|
| 2-5 | 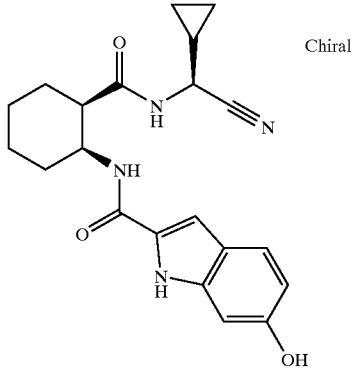 | Chiral | N-[(1S,2R)-2-({[[(S)-cyano(cyclopropyl)methyl]amino}carbonyl)cyclohexyl]-6-hydroxy-1H-indole-2-carboxamide | B-2 | 380.446 | 380 |
| 2-6 | 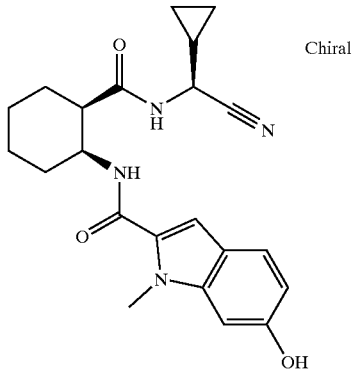 | Chiral | N-[(1S,2R)-2-({[[(S)-cyano(cyclopropyl)methyl]amino}carbonyl)cyclohexyl]-6-hydroxy-1-methyl-1H-indole-2-carboxamide | B-2 | 394.472 | 394 |
| 2-7 | 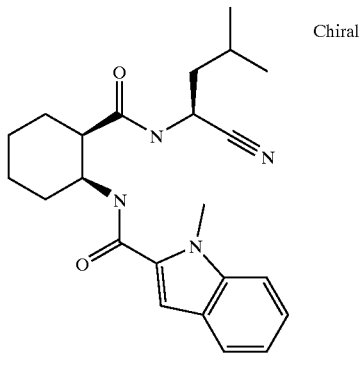 | Chiral | N-[(1S,2R)-2-({[[(1S)-1-cyano-3-methylbutyl]amino}carbonyl)cyclohexyl]-1-methyl-1H-indole-2-carboxamide | B-2 | 394.516 | 394 |
| 2-8 | 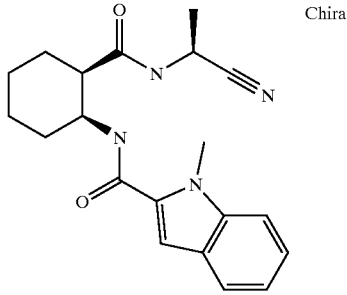 | Chiral | N-[(1S,2R)-2-({[[(1S)-1-cyanoethyl]amino}carbonyl)cyclohexyl]-1-methyl-1H-indole-2-carboxamide | B-2 | 352.436 | 352 |

COMPOUND TABLE 2-continued

| Cpd # | Structure | Compound Name | Method | MW | M/S |
|---|---|---|---|---|---|
| 2-9 | 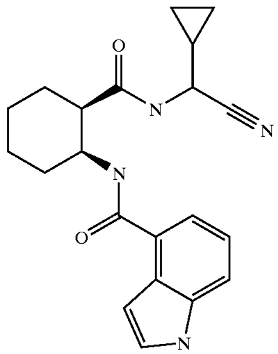 | N-[(1S,2R)-2-({[cyano(cyclopropyl)methyl]amino}carbonyl)cyclohexyl]-1H-indole-4-carboxamide | A | 364.447 | 364 |
| 2-10 | Chiral | N-((1S,2R)-2-{[(cyanomethyl)amino]carbonyl}cyclohexyl)-5-fluoro-1-methyl-1H-indole-2-carboxamide | A | 356.399 | 356 |
| 2-11 | Chiral | N-[(1S,2R)-2-({[(1R)-1-cyano-2-hydroxyethyl]amino}carbonyl)cyclohexyl]-1-methyl-1H-indole-2-carboxamide | B-3 | 368.435 | 368 |
| 2-12 | Chiral | N-[(1S,2R)-2-({[(S)-cyano(cyclopropyl)methyl]amino}carbonyl)cyclohexyl]-5-fluoro-1-methyl-1H-indole-2-carboxamide | B-2 | 396.463 | 396 |

COMPOUND TABLE 2-continued

| Cpd # | Structure | Compound Name | Method | MW | M/S |
|---|---|---|---|---|---|
| 2-13 | 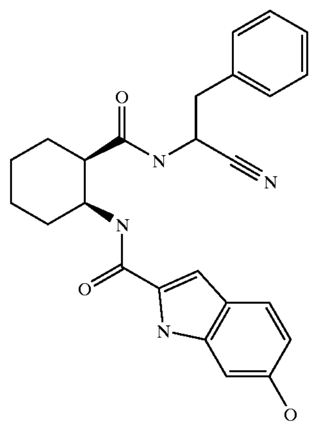 | N-((1S,2R)-2-{[(1-cyano-2-phenylethyl)amino]carbonyl}cyclohexyl)-6-hydroxy-1H-indole-2-carboxamide | B-2 | 430.505 | 430 |
| 2-14 | 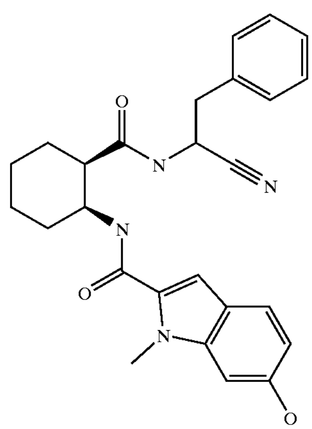 | N-((1S,2R)-2-{[(1-cyano-2-phenylethyl)amino]carbonyl}cyclohexyl)-6-hydroxy-1-methyl-1H-indole-2-carboxamide | B-2 | 444.532 | 444 |
| 2-15 | 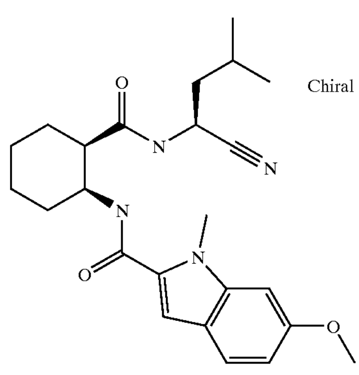 | N-[(1S,2R)-2-({[(1S)-1-cyano-3-methylbutyl]amino}carbonyl)cyclohexyl]-6-methoxy-1-methyl-1H-indole-2-carboxamide | B-2 | 424.542 | 424 |

COMPOUND TABLE 2-continued

| Cpd # | Structure | | Compound Name | Method | MW | M/S |
|---|---|---|---|---|---|---|
| 2-16 | 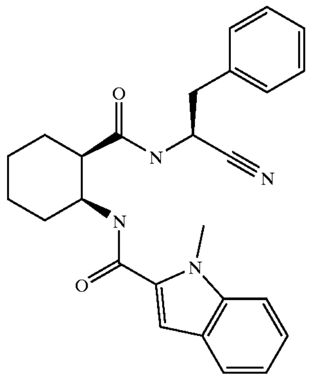 | Chiral | N-[(1S,2R)-2-({[(1S)-1-cyano-2-phenylethyl]amino}carbonyl)cyclohexyl]-1-methyl-1H-indole-2-carboxamide | B-2 | 428.533 | 428 |
| 2-17 | 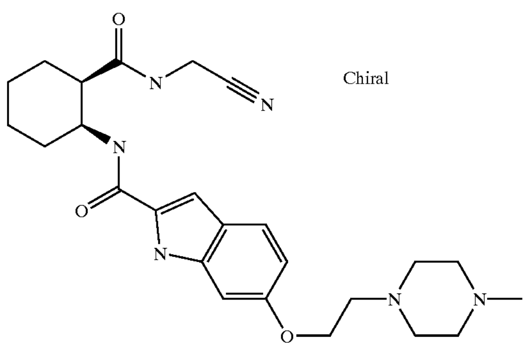 | Chiral | N-((1S,2R)-2-{[(cyanomethyl)amino]carbonyl}cyclohexyl)-6-[2-(4-methylpiperazin-1-yl)ethoxy]-1H-indole-2-carboxamide | A | 466.583 | 466 |
| 2-18 | 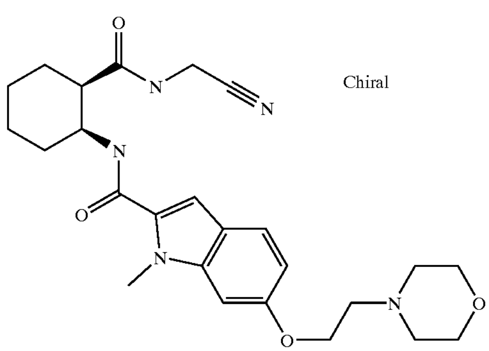 | Chiral | N-((1S,2R)-2-{[(cyanomethyl)amino]carbonyl}cyclohexyl)-1-methyl-6-(2-morpholin-4-ylethoxy)-1H-indole-2-carboxamide | A | 467.567 | 467 |
| 2-19 | 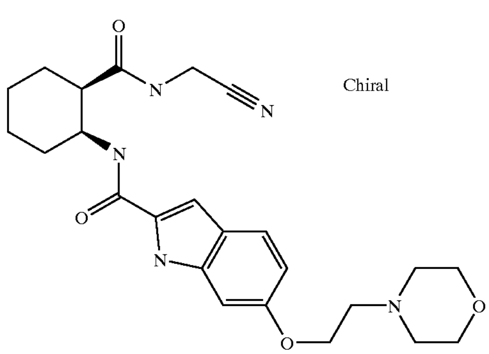 | Chiral | N-((1S,2R)-2-{[(cyanomethyl)amino]carbonyl}cyclohexyl)-6-(2-morpholin-4-ylethoxy)-1H-indole-2-carboxamide | A | 453.54 | 453 |

COMPOUND TABLE 2-continued

| Cpd # | Structure | | Compound Name | Method | MW | M/S |
|---|---|---|---|---|---|---|
| 2-20 | 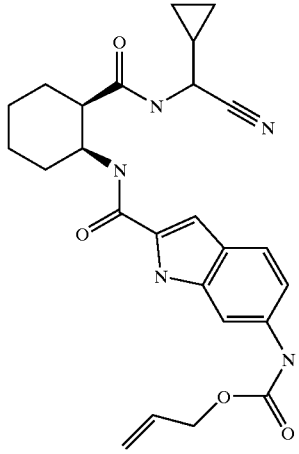 | | allyl 2-({[(1S,2R)-2-({[cyano(cyclopropyl)methyl]amino}carbonyl)cyclohexyl]amino}carbonyl)-1H-indol-6-ylcarbamate | A | 463.535 | 463 |
| 2-21 | 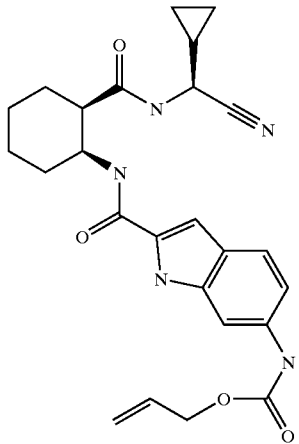 | Chiral | allyl 2-({[(1S,2R)-2-({[(S)-cyano(cyclopropyl)methyl]amino}carbonyl)cyclohexyl]amino}carbonyl)-1H-indol-6-yl-carbamate | A | 463.535 | 463 |
| 2-22 | 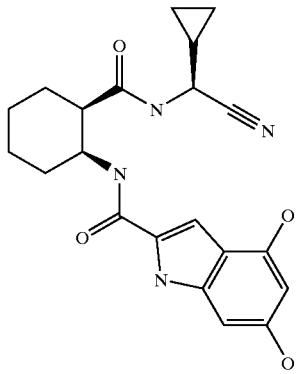 | Chiral | N-[(1S,2R)-2-({[(S)-cyano(cyclopropyl)methyl]amino}carbonyl)cyclohexyl]-4,6-dimethoxy-1H-indole-2-carboxamide | A | 424.498 | 424 |

COMPOUND TABLE 2-continued

| Cpd # | Structure | Compound Name | Method | MW | M/S |
|---|---|---|---|---|---|
| 2-23 | 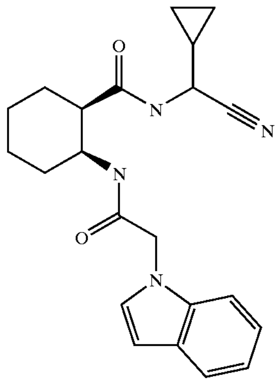 | (1R,2S)-N-[cyano(cyclopropyl)methyl]-2-[(1H-indol-1-ylacetyl)amino]cyclohexanecarboxamide | A | 378.473 | 378 |
| 2-24 | Chiral | N-[(1S,2R)-2-({[(S)-cyano(cyclopropyl)methyl]amino}carbonyl)cyclohexyl]quinoline-2-carboxamide | A | 376.458 | 376 |
| 2-25 | Chiral | N-((1S,2R)-2-{[(cyanomethyl)amino]carbonyl}cyclohexyl)-1H-indazole-5-carboxamide | A | 325.37 | 325 |

COMPOUND TABLE 3

| Cpd. # | Structure | Name | Method | MW | MS |
|---|---|---|---|---|---|
| 3-1 | Chiral | N-[(1S,2R)-2-({[(S)-cyano(cyclopropyl)methyl]amino}carbonyl)cyclohexyl]-6-[(methylsulfonyl)amino]-1H-indole-2-carboxamide | A | 457.552 | 457 |

COMPOUND TABLE 3-continued

| Cpd. # | Structure | | Name | Method | MW | MS |
|---|---|---|---|---|---|---|
| 3-2 | 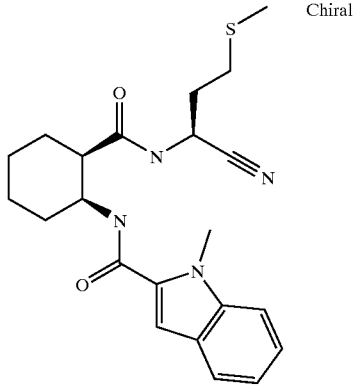 | Chiral | N-[(1S,2R)-2-({[(1S)-1-cyano-3-(methylthio)propyl]amino}carbonyl)cyclohexyl]-1-methyl-1H-indole-2-carboxamide | B-2 | 412.555 | 412 |
| 3-3 | 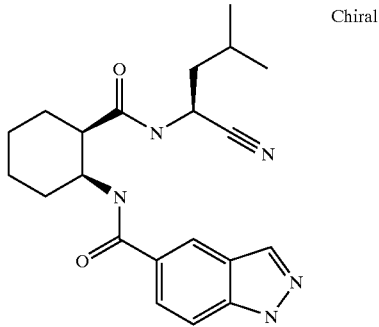 | Chiral | N-[(1S,2R)-2-({[(1S)-1-cyano-3-methylbutyl]amino}carbonyl)cyclohexyl]-1H-inadazole-5-carboxamide | B-2 | 381.477 | 381 |
| 3-4 | 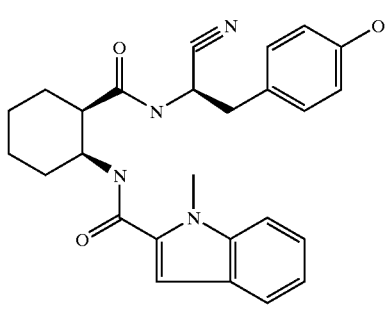 | Chiral | N-[(1S,2R)-2-({[(1R)-1-cyano-2-(4-hydroxyphenyl)ethyl]amino}carbonyl)cyclohexyl]-1-methyl-1H-indole-2-carboxamide | B-2 | 444.532 | 444 |
| 3-5 | 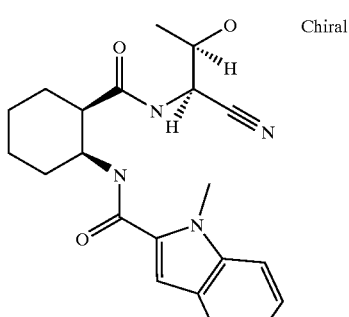 | Chiral | N-[(1S,2R)-2-({[(1R,2R)-1-cyano-2-hydroxypropyl]amino}carbonyl)cyclohexyl]-1-methyl-1H-indole-2-carboxamide | B-2 | 382.461 | 382 |

COMPOUND TABLE 3-continued

| Cpd. # | Structure | Name | Method | MW | MS |
|---|---|---|---|---|---|
| 3-6 | Chiral | tert-butyl (3S)-3-cyano-3-{[((1R,2S)-2-{[(1-methyl-1H-indol-2-yl)carbonyl]amino}cyclohexyl)carbonyl]amino}propanoate | B-2 | 452.552 | 452 |
| 3-7 | Chiral | N-[(1S,2R)-2-({[(1S)-1-cyanobutyl]amino}carbonyl)cyclohexyl]-1-methyl-1H-indole-2-carboxamide | B-2 | 380.489 | 380 |
| 3-8 | Chiral | tert-butyl (4S)-4-cyano-4-{[((1R,2S)-2-{[(1-methyl-1H-indol-2-yl)carbonyl]amino}cyclohexyl)carbonyl]amino}-butanoate | B-2 | 466.579 | 466 |

COMPOUND TABLE 3-continued
| Cpd. # | Structure | Name | Method | MW | MS |
|---|---|---|---|---|---|
| 3-9 | 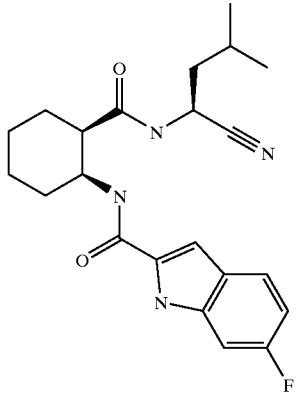 Chiral | N-[(1S,2R)-2-({[(1S)-1-cyano-3-methylbutyl]amino}carbonyl)cyclohexyl]-6-fluoro-1H-indole-2-carboxamide | B-2 | 398.479 | 398 |
| 3-10 | 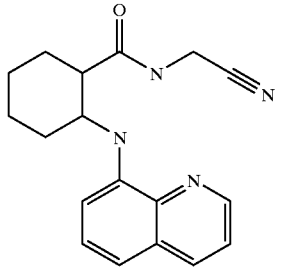 | N-(cyanomethyl)-2-(quinolin-8-ylamino)cyclohexane-carboxamide | D | 308.383 | 308 |
COMPOUND TABLE 4
| Cpd.# | Structure | Example | MW | MS |
|---|---|---|---|---|
| 4-1 | 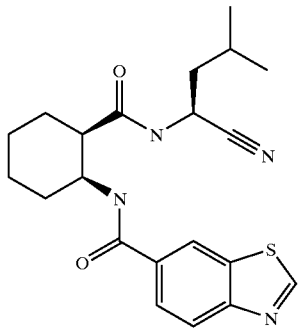 Chiral | 10 | 398.528 | 398 |

COMPOUND TABLE 4-continued

| Cpd.# | Structure | Example | MW | MS |
|---|---|---|---|---|
| 4-2 | 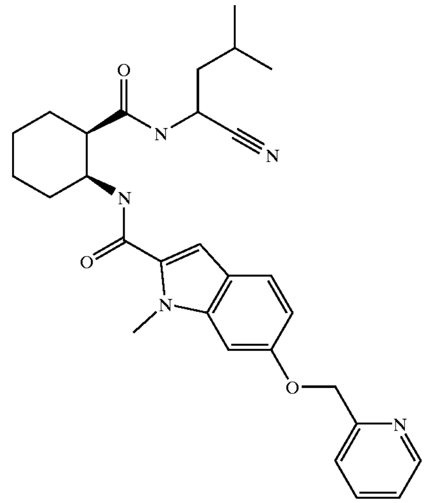 | 12 | 501.627 | 502 |
| 4-3 | 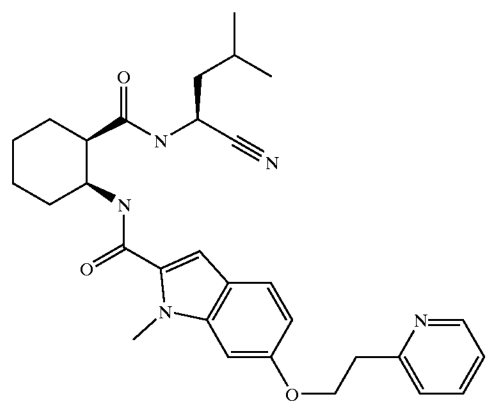 | 12 | 515.654 | 515 |
| 4-4 | 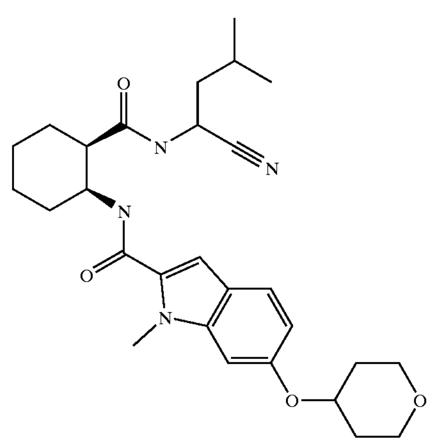 | 12 | 494.632 | 494 |

COMPOUND TABLE 4-continued
| Cpd.# | Structure | Example | MW | MS |
|---|---|---|---|---|
| 4-5 | 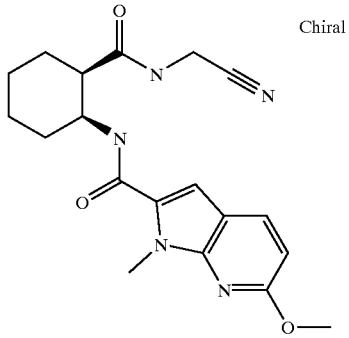 | A | 369.423 | 369 |
| 4-6 | 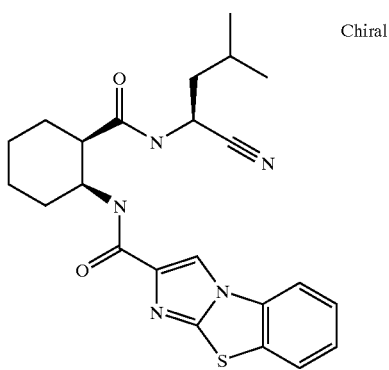 | 10 | 437.565 | 437 |
| 4-7 | 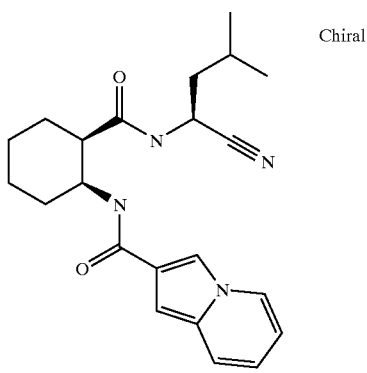 | 10 | 380.489 | 380 |
| 4-8 | 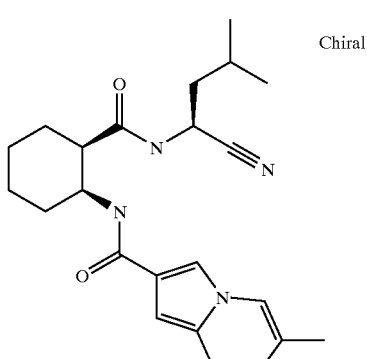 | 10 | 394.516 | 394 |

COMPOUND TABLE 4-continued

| Cpd.# | Structure | Example | MW | MS |
|---|---|---|---|---|
| 4-9 | 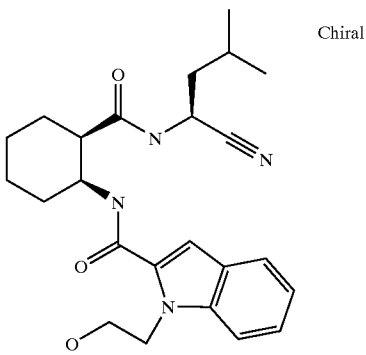 | 11 | 424.542 | 424 |

BIOLOGICAL EXAMPLES

Example 1
Determination of Inhibition of Cathepsin K, O and S

The inhibitory activity of the compounds against cathepsin K, S, L and B was tested at room temperature in 96-wells opaque white polystyrene plates (Costar). The cathepsin K inhibitory activity was tested as follows:

5 μl of an inhibitor diluted in 5 mM sodium phosphate, NaCl 15 mM pH 7.4 containing 1% DMSO (final concentrations: 10–0.0001 μM) were preincubated for 10 min with 35 μl of human recombinant cathepsin K (final concentration: 1 nM) diluted in assay buffer (100 mM sodium acetate pH 5.5 containing 5 mM EDTA and 20 mM cysteine). After addition of 10 μl of the fluorogenic substrate Z-Leu-Arg-MCA diluted in assay buffer (final concentration: 5 μM), increase of fluorescence (excitation at 390 nm and emission at 460 nm) was measured for 7.5 min every 45 sec. The initial velocity (RFU/min) was derived from the linear fit of the 11 reading points.

The cathepsin B inhibitory activity was assayed under the same conditions as the cathepsin K inhibitory activity using human liver cathepsin B (Calbiochem) at a final concentration of 1 nM.

The cathepsin L inhibitory activity was assayed under the same conditions as the cathepsin K inhibitory activity using human liver cathepsin L (Calbiochem) at a final concentration of 3 nM.

Cathepsin S inhibitory activity was assayed analogeously to the cathepsin K inhibitory activity, except that the buffer was 100 mM potassium phosphate, 5 mM EDTA, 5 mM DTT (freshly added), 0.01% Triton X-100, pH 6.5 and the fluorogenic substrate was Z-Val-Val-Arg-MCA (Bachem) (final concentration: 20 μM). Human recombinant cathepsin S (Wiederanders et al., Eur. J. Biochem. 1997, 250, 745–750) was used at a final concentration of 0.5 nM.

Biological Data

| Compound Example | Cathepsin K IC$_{50}$ (□Mol/l) |
|---|---|
| 1 | 0.018 □M |
| 2 | 0.0454 □M |
| 4 | 0.0964 □M |
| 5 | 0.0600 □M |
| 11 | 0.003 |

Formulation Examples

Example A

Tablets containing the following ingredients can be manufactured in a conventional manner:

| Ingredients | Per tablet |
|---|---|
| Compound of formula I | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

Example C

Injection solutions can have the following composition:

| | |
|---|---|
| Compound of formula I | 3.0 mg |
| Gelatine | 150.0 mg |
| Phenol | 4.7 mg |
| Water for injection solutions | ad 1.0 ml |

What is claimed is:

1. Compounds of formula (I)

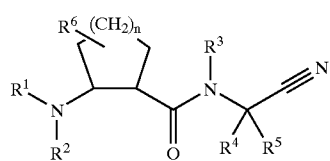

wherein
R¹ is heteroaryl, (CR'R")$_m$—CO—R$^a$ or —S(O)$_p$—R$^a$;
  wherein:
  R' and R" are independently hydrogen or lower alkyl;
  m is zero or one;
  p is one or two;
  R$^a$ is heteroaryl, heteroaryl-lower-alkyl, or heteroaryl-lower-alkoxy wherein the heteroaryl in each of the preceding is selected from the group consisting of indolyl, pyridyl, quinolinyl, isoquinolinyl, N-oxo-quinolinyl, N-oxo-isoquinolinyl, naphthyridinyl, pyrazolyl, indazolyl, furo[2,3-b]pyridinyl, furo[2,3-c]pyridinyl, furo[3,2-c]pyridinyl, furo[3,2-b]pyridinyl, 1H-pyrrolo[3,2-b]pyridinyl, 1H-pyrrolo[2,3-b]pyridinyl, 1H-pyrrolo[3,2-c]pyridinyl, 1H-pyrrolo[2,3-c]pyridinyl, 1H-pyrazolo[3,4-b]pyridine, 1H-pyrazolo[3,4-c]pyridine, 1H-pyrazolo[4,3-b]pyridine, 1H-pyrazolo[4,3-c]pyridine, benzothiazolyl, azaindolyl, imidazo[2,1-b]benzothiazolyl and indolizinyl, each optionally substituted;
R² is hydrogen or lower-alkyl
R³ is hydrogen or lower-alkyl
R⁴ is hydrogen or lower-alkyl,
R⁵ is hydrogen, lower-alkyl, heteroalkyl, alkoxyacylalkyl, cycloalkyl, cycloalkyl-loweralkyl, aryl aralkyl, heteroaryl or heteroaryl-loweralkyl;
R⁶ is hydrogen or alkyl; and
n is an integer from one to three;
and pharmaceutically acceptable salts and/or pharmaceutically acceptable esters thereof.

2. The compound of claim 1, wherein R¹ is C(O)—R$^a$.
3. The compound of claim 2, wherein R² is hydrogen.
4. The compound of claim 3, wherein R³ is hydrogen.
5. The compound of claim 4, wherein R⁴ and R⁵ are hydrogen.
6. The compound of claim 4, wherein R⁴ is hydrogen and R⁵ is cycloalkyl.
7. The compound of claim 6, wherein R⁵ is cyclopropyl.
8. The compound of claim 4, wherein R$^a$ is indolyl, pyridyl, quinolinyl, isoquinolinyl, N-oxo-quinolinyl, N-oxo-isoquinolinyl, pyrazolyl or indazolyl, each optionally substituted.
9. The compound of claim 8, wherein R$^a$ is indolyl or indazolyl, each optionally substituted.
10. The compound of claim 8, wherein R$^a$ is 2-indolyl, 5-fluoro-indol-2-yl, 1-methyl-indol-2-yl, 5-chloro-indol-1-yl or 5-indolyl, each optionally substituted.
11. The compound of claim 9, wherein R$^a$ is optionally substituted N-alkyl-indolyl.
12. The compound of claim 8, wherein R⁴ and R⁵ are hydrogen.
13. The compound of claim 8, wherein R⁴ is hydrogen and R⁵ is cycloalkyl.
14. The compound of claim 13, wherein, R⁵ is cyclopropyl.
15. The compounds of claim 11 or 12, wherein n is 2.
16. The compound of claim 4, wherein n is 2.
17. The compound of claim 16, wherein R$^a$ is an indolyl or indazolyl, each optionally substituted.
18. The compound of claim 17, wherein R⁴ is hydrogen and R⁵ is cycloalkyl.
19. The compound of claim 18, wherein R⁵ is cyclopropyl.
20. The compound of claim 17, which is N-[(1S,2R)-2-({[(S)-cyano(cyclopropyl)methyl]amino}carbonyl)cyclohexyl]-1-methyl-1H-indole-2-carboxamide.
21. The compound of claim 17, wherein R⁴ is hydrogen and R⁵ is alkyl.
22. The compound of claim 21, wherein R⁴ is isobutyl, i.e., N-[(1S,2R)-2-({[(1S)-1-cyano-3-methylbutyl]amino}carbonyl)cyclohexyl]-1-methyl-1H -indole-2-carboxamide.
23. The compound of claim 1, wherein R¹ is heteroaryl.
24. The compound of claim 23, wherein R² and R³ is hydrogen.
25. The compound of claim 24, wherein n is two.
26. The compound of claim 25, wherein R¹ is indolyl or indazolyl, each optionally substituted.
27. The compound of claim 1, wherein R² and R³ are hydrogen.
28. The compound of claim 27, wherein n is two.
29. The compound of claim 28, wherein R⁴ is hydrogen and R⁵ is alkyl or cycloalkyl.
30. The compound of claim 29, wherein R⁵ is cyclopropyl.
31. The compound of claim 30, wherein R⁵ is isobutyl.
32. The compound of claim 30 or 31 wherein R¹ is C(O)—R$^a$.
33. A method for preparing a compound of claim 1 comprising:
  a) reacting a compound of formula (II)

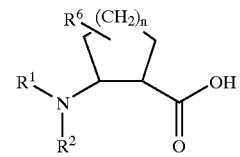

with a compound of formula (III)

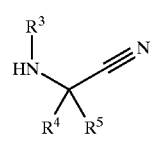

wherein R¹, R², R³, R⁴, R⁵, R⁶ and n are as defined in claim 1, or
  b) reacting a compound of formula (IV)

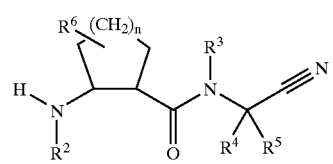

with a compound of formula (V) or (VI)

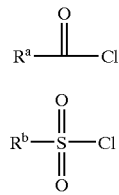
(V)

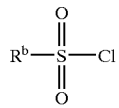
(VI)

wherein $R^2$, $R^3$, $R^4$, $R^5$, $R^6$, $R^a$, $R^b$ and n are as defined in claim 1.

34. A method of preparing a compound of claim 1 comprising treating a compound of Formula (XI)

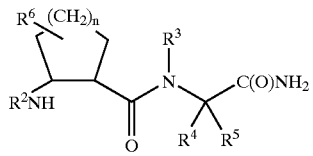
(XI)

with a dehydrating agent selected from trifluoroacetic anhydride, Burgess reagent, TsCl, $SOCl_2$, $COCl_2$, $P_2O_5$ and $POCl_3$, wherein $R^2$, $R^3$, $R^4$, $R^5$, $R^6$ and n are as defined in claim 1.

35. A pharmaceutical composition comprising a compound of claim 1 and a pharmaceutically acceptable carrier and/or adjuvant.

36. A method for the treatment of osteoporosis, breast tumor, breast tumor-derived bone metastasis, instable angina pectoris and/or plaque rupture in a human being or animal, which method comprises administering a therapeutically effective amount a compound according to claim 1 to the human being or animal.

* * * * *